US009861622B2

(12) United States Patent
Rader

(10) Patent No.: US 9,861,622 B2
(45) Date of Patent: *Jan. 9, 2018

(54) METHODS FOR TREATING DISORDERS OR DISEASES ASSOCIATED WITH HYPERLIPIDEMIA AND HYPERCHOLESTEROLEMIA WHILE MINIMIZING SIDE-EFFECTS

(71) Applicant: The Trustees of the University of Pennsylvania, Philadelphia, PA (US)

(72) Inventor: Daniel J. Rader, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/218,670

(22) Filed: Jul. 25, 2016

(65) Prior Publication Data

US 2016/0331739 A1 Nov. 17, 2016

Related U.S. Application Data

(63) Continuation of application No. 15/155,647, filed on May 16, 2016, now Pat. No. 9,433,617, which is a continuation of application No. 14/959,756, filed on Dec. 4, 2015, now Pat. No. 9,364,470, which is a continuation of application No. 14/075,483, filed on Nov. 8, 2013, now Pat. No. 9,265,758, which is a continuation of application No. 13/046,118, filed on Mar. 11, 2011, now Pat. No. 8,618,135, which is a continuation of application No. 10/591,923, filed as application No. PCT/US2005/007435 on Mar. 7, 2005, now Pat. No. 7,932,268.

(60) Provisional application No. 60/550,915, filed on Mar. 5, 2004.

(51) Int. Cl.
| A61K 31/4468 | (2006.01) |
| A61K 31/405 | (2006.01) |
| A61K 31/445 | (2006.01) |
| A61K 31/21 | (2006.01) |
| A61K 9/00 | (2006.01) |
| A61K 31/52 | (2006.01) |

(52) U.S. Cl.
CPC ........ A61K 31/4468 (2013.01); A61K 9/0053 (2013.01); A61K 31/21 (2013.01); A61K 31/405 (2013.01); A61K 31/445 (2013.01); A61K 31/52 (2013.01)

(58) Field of Classification Search
CPC .............. A61K 31/4468; A61K 9/0053; A61K 31/445
See application file for complete search history.

(56) References Cited

U.S. PATENT DOCUMENTS

| 3,983,140 A | 9/1976 | Endo et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,647,576 A | 3/1987 | Hoefle et al. |
| 4,686,237 A | 8/1987 | Anderson |
| 4,716,175 A | 12/1987 | Hoefle et al. |
| 4,871,721 A | 10/1989 | Biller |
| 4,924,024 A | 5/1990 | Biller |
| 5,015,644 A | 5/1991 | Roth et al. |
| 5,026,554 A | 6/1991 | Bartizal et al. |
| 5,117,080 A | 5/1992 | Lee et al. |
| 5,510,379 A | 4/1996 | Lee et al. |
| 5,595,872 A | 1/1997 | Wetterau, II et al. |
| 5,684,014 A | 11/1997 | Muller et al. |
| 5,712,279 A | 1/1998 | Biller et al. |
| 5,712,396 A | 1/1998 | Magnin et al. |
| 5,739,135 A | 4/1998 | Biller et al. |
| 5,760,246 A | 6/1998 | Biller et al. |
| 5,767,115 A | 6/1998 | Rosenblum et al. |
| 5,786,361 A | 7/1998 | Muller et al. |
| 5,789,197 A | 8/1998 | Wetterau, II et al. |
| 5,811,429 A | 9/1998 | Connell et al. |
| 5,827,875 A | 10/1998 | Dickson, Jr. et al. |
| 5,883,109 A | 3/1999 | Gregg et al. |
| 5,885,983 A | 3/1999 | Biller et al. |
| 5,952,498 A | 9/1999 | Lenfers et al. |
| 5,990,110 A | 11/1999 | Firestone |
| 6,034,115 A | 3/2000 | Connell et al. |
| 6,057,339 A | 5/2000 | Gregg |
| 6,066,650 A | 5/2000 | Biller et al. |
| 6,066,653 A | 5/2000 | Gregg et al. |
| 6,114,341 A | 9/2000 | Muller et al. |
| 6,121,283 A | 9/2000 | Chang et al. |
| 6,140,343 A | 10/2000 | DeNinno et al. |
| 6,194,454 B1 | 2/2001 | Dow |

(Continued)

FOREIGN PATENT DOCUMENTS

| AU | 727895 | 7/1998 |
| CA | 2091102 | 9/1993 |

(Continued)

OTHER PUBLICATIONS

Ex. 2018 to Updated List of Patent Owner's Exhibits dated Jun. 7, 2016, IPR2015-01835, "Michael Mayersohn, Designing a Dosage Regimen: Drug Therapy, Clin. Ther., vol. 10, No. 10 (Oct. 1980)".

(Continued)

*Primary Examiner* — Shirley V Gembeh
(74) *Attorney, Agent, or Firm* — Haug Partners LLP

(57) ABSTRACT

The present invention provides methods and compositions for treating hyperlipidemia and/or hypercholesterolemia comprising administering to the subject an effective amount of an MTP inhibitor to inhibit hyperlipidemia and/or hypercholesterolemia in said subject, wherein said administration comprises an escalating series of doses of the MTP inhibitor. In some embodiments the method comprises administering at least three step-wise, increasing dosages of the MTP inhibitor to the subject. In some embodiments, the method further comprises the administration of one or more other lipid modifying compounds.

14 Claims, No Drawings

(56) References Cited

U.S. PATENT DOCUMENTS

| | | |
|---|---|---|
| 6,245,775 B1 | 6/2001 | Muller et al. |
| 6,265,431 B1 | 7/2001 | Muller et al. |
| 6,297,233 B1 | 10/2001 | Stein et al. |
| 6,344,450 B1 | 2/2002 | Bisacchi et al. |
| 6,479,503 B2 | 11/2002 | Muller et al. |
| 6,492,365 B1 | 12/2002 | Wetterau, II et al. |
| 6,498,156 B2 | 12/2002 | Glombik et al. |
| 6,582,698 B1 | 6/2003 | Dedrick et al. |
| 6,620,821 B2 | 9/2003 | Robl |
| 6,627,636 B2 | 9/2003 | Robl |
| 6,720,351 B2 | 4/2004 | Bertinato et al. |
| 6,774,236 B1 | 8/2004 | Lenfers et al. |
| 6,812,345 B2 | 11/2004 | Robl et al. |
| 6,846,836 B2 | 1/2005 | Hamann et al. |
| 6,858,622 B2 | 2/2005 | Muller et al. |
| 6,875,782 B2 | 4/2005 | Cheng et al. |
| 6,884,812 B2 | 4/2005 | Glombik et al. |
| 6,916,809 B2 | 7/2005 | Chen et al. |
| 6,916,813 B2 | 7/2005 | Atwal et al. |
| 6,949,572 B2 | 9/2005 | Bertinato et al. |
| 6,979,692 B2 | 12/2005 | Bertinato et al. |
| 7,053,080 B2 | 5/2006 | Davis et al. |
| 7,056,906 B2 | 6/2006 | Strony |
| 7,358,254 B2 | 4/2008 | Robl et al. |
| 7,394,501 B2 | 7/2008 | Iwata et al. |
| 7,645,732 B2 | 1/2010 | Ye et al. |
| 7,932,268 B2 | 4/2011 | Rader |
| 8,618,135 B2 | 12/2013 | Rader |
| 9,265,758 B2 | 2/2016 | Rader |
| 2002/0035064 A1 | 3/2002 | Robl et al. |
| 2002/0045271 A1 | 4/2002 | Hussain et al. |
| 2003/0069221 A1 | 4/2003 | Kosoglou et al. |
| 2003/0109543 A1 | 6/2003 | Ogletree |
| 2003/0153541 A1 | 8/2003 | Dudley et al. |
| 2003/0162788 A1 | 8/2003 | Thomas et al. |
| 2003/0187053 A1 | 10/2003 | Bertinato et al. |
| 2004/0014748 A1 | 1/2004 | Grutzmann et al. |
| 2004/0058908 A1 | 3/2004 | Keller et al. |
| 2005/0075367 A1 | 4/2005 | Hagiwara et al. |
| 2005/0090426 A1 | 4/2005 | Blumberg |
| 2005/0101561 A1 | 5/2005 | Tunac |
| 2006/0069161 A1 | 3/2006 | Lee et al. |
| 2006/0135460 A1 | 6/2006 | Widder et al. |
| 2006/0153913 A1 | 7/2006 | Yamane et al. |
| 2006/0160834 A1 | 7/2006 | Fong et al. |
| 2006/0166999 A1 | 7/2006 | Grutzmann et al. |
| 2006/0205726 A1 | 9/2006 | Hagiwara et al. |
| 2006/0211020 A1 | 9/2006 | Farrer et al. |
| 2006/0211762 A1 | 9/2006 | Rongen et al. |
| 2006/0252733 A1 | 11/2006 | Jansen |
| 2006/0270655 A1 | 11/2006 | Swick et al. |
| 2007/0027093 A1 | 2/2007 | Ogawa et al. |
| 2007/0032404 A1 | 2/2007 | Sweet |
| 2007/0088089 A1 | 4/2007 | Wisler |
| 2007/0093468 A1 | 4/2007 | Wisler |
| 2007/0093527 A1 | 4/2007 | Wisler |
| 2007/0098778 A1 | 5/2007 | Borsadia |
| 2007/0099884 A1 | 5/2007 | Erondu et al. |
| 2008/0016127 A1 | 1/2008 | Field |
| 2008/0033019 A1 | 2/2008 | Stamler |
| 2008/0051427 A1 | 2/2008 | Schuckler |
| 2008/0103122 A1 | 5/2008 | Veltri |
| 2008/0161279 A1 | 7/2008 | Wisler |
| 2008/0175864 A1 | 7/2008 | Ye et al. |
| 2008/0241869 A1 | 10/2008 | Davis |
| 2008/0248070 A1 | 10/2008 | Tunac |
| 2008/0253985 A1 | 10/2008 | Wisler |
| 2008/0255084 A1 | 10/2008 | Webb |
| 2008/0280992 A1 | 11/2008 | Kunz et al. |
| 2009/0042835 A1 | 2/2009 | Davis |
| 2009/0042941 A1 | 2/2009 | Rader |
| 2009/0054393 A1 | 2/2009 | Wisler |
| 2009/0093527 A1 | 4/2009 | Li et al. |
| 2010/0273829 A1 | 10/2010 | Wisler |
| 2012/0035204 A1 | 2/2012 | Sasiela |

FOREIGN PATENT DOCUMENTS

| | | |
|---|---|---|
| CA | 2291471 | 6/2000 |
| CA | 2325201 | 5/2001 |
| DE | 19951022 | 4/2001 |
| EP | 0142146 | 5/1985 |
| EP | 0221025 | 5/1987 |
| EP | 0325130 | 7/1989 |
| EP | 0705831 | 4/1996 |
| EP | 0779276 | 6/1997 |
| EP | 0779279 | 6/1997 |
| EP | 0799828 | 10/1997 |
| EP | 0802198 | 10/1997 |
| EP | 1099442 | 5/2001 |
| EP | 1181954 | 2/2002 |
| FR | 2596393 | 10/1987 |
| GB | 2205837 | 12/1988 |
| JP | 2002/220345 | 9/1990 |
| JP | 2003/321424 A | 11/2003 |
| WO | WO-1986/003488 | 6/1986 |
| WO | WO-1986/007054 | 12/1986 |
| WO | WO-1996/026205 | 8/1996 |
| WO | WO-1996/026946 A1 | 9/1996 |
| WO | WO-1996/040640 | 12/1996 |
| WO | WO-1997/041111 | 11/1997 |
| WO | WO-1998/003069 | 1/1998 |
| WO | WO-1998/003174 | 1/1998 |
| WO | WO-1998/023593 | 6/1998 |
| WO | WO-1998/027979 | 7/1998 |
| WO | WO-1998/031225 | 7/1998 |
| WO | WO-1998/031366 | 7/1998 |
| WO | WO-1998/031367 | 7/1998 |
| WO | WO-1998/050028 | 11/1998 |
| WO | WO-2000/038725 | 7/2000 |
| WO | WO-2001/008679 | 2/2001 |
| WO | WO-2004/008861 A1 | 1/2004 |
| WO | WO-2004/028544 | 4/2004 |
| WO | WO-2004/110368 | 12/2004 |
| WO | WO-2004/110375 | 12/2004 |
| WO | WO-2005/000217 | 1/2005 |
| WO | WO-2005/033100 A1 | 4/2005 |
| WO | WO-2005/051382 | 6/2005 |
| WO | WO-2005/072740 | 8/2005 |
| WO | WO-2005/084666 A1 | 9/2005 |
| WO | WO-2005/085466 | 9/2005 |
| WO | WO-2005/087234 A1 | 9/2005 |
| WO | WO-2005/087324 | 9/2005 |
| WO | WO-2005/094864 | 10/2005 |
| WO | WO-2005/097131 | 10/2005 |
| WO | WO-2006/046623 | 5/2006 |
| WO | WO-2006/062748 | 6/2006 |
| WO | WO-2006/063128 | 6/2006 |
| WO | WO-2006/108666 | 10/2006 |
| WO | WO-2006/111238 | 10/2006 |
| WO | WO-2007/047724 A2 | 4/2007 |
| WO | WO-2007/047880 | 4/2007 |
| WO | WO-2008/012056 | 1/2008 |
| WO | WO-2008/021353 | 2/2008 |
| WO | WO-2008/030382 | 3/2008 |
| WO | WO-2008/072061 A1 | 6/2008 |
| WO | WO-2008/075949 | 6/2008 |
| WO | WO-2008/079398 A1 | 7/2008 |
| WO | WO-2008/090198 | 7/2008 |
| WO | WO-2008/115574 | 9/2008 |

OTHER PUBLICATIONS

Ex. 2019 to Updated List of Patent Owner's Exhibits dated Jun. 7, 2016, IPR2015-01835, "Peter Jones et al., Comparative Dose Efficacy Study of Atorvastatin Versus Simvastatin, Pravastatin, Lovastatin, and Fluvastatin in Patients With Hypercholesterolemia (The CURVES Study, Am. J. Cardiol., vol. 81 (Mar. 1, 1998)".

Ex. 2020 to Updated List of Patent Owner's Exhibits dated Jun. 7, 2016, IPR2015-01835, "Jeffrey A. Robl et al., A Novel Series of Highly Potent Benzimidazole-Based Microsomal Triglyceride Transfer Protein Inhibitors, J. Med. Chem., vol. 44, No. 6 (Mar. 15, 2001)".

(56) References Cited

OTHER PUBLICATIONS

Ex. 2021 to Updated List of Patent Owner's Exhibits dated Jun. 7, 2016, IPR2015-01835, "Deposition Transcript of Michael Mayersohn, Ph. D. (May 16, 2016)".
Ex. 2022 to Updated List of Patent Owner's Exhibits dated Jun. 7, 2016, IPR2015-01835, "Deposition Transcript of Randall M. Zusman, M.D. (May 19, 2016)".
Ex. 2023 to Updated List of Patent Owner's Exhibits dated Jun. 7, 2016, IPR2015-01835, "Declaration of Dr. Frank Sacks, M.D."
Ex. 2024 to Updated List of Patent Owner's Exhibits dated Jun. 7, 2016, IPR2015-01835, "Declaration of Dr. Thomas A. Baillie, Ph.D., D.SC."
Ex. 2025 to Updated List of Patent Owner's Exhibits dated Jun. 7, 2016, IPR2015-01835, "Declaration of S. David Kimball, Ph.D."
Ex. 2026 to Updated List of Patent Owner's Exhibits dated Jun. 7, 2016, IPR2015-01835, "Declaration of Daniel J. Rader, M.D."
Ex. 2027 to Updated List of Patent Owner's Exhibits dated Jun. 7, 2016, IPR2015-01835, "Dr. Frank Sacks, M.D., curriculum vitae".
Ex. 2028 to Updated List of Patent Owner's Exhibits dated Jun. 7, 2016, IPR2015-01835, "Dr. Thomas A. Baillie, Ph.D., D.SC., curriculum vitae".
Ex. 2029 to Updated List of Patent Owner's Exhibits dated Jun. 7, 2016, IPR2015-01835, "S. David Kimball, Ph.D., curriculum vitae".
Ex. 2030 to Updated List of Patent Owner's Exhibits dated Jun. 7, 2016, IPR2015-01835, "Daniel J. Rader, M.D., curriculum vitae".
Ex. 2031 to Updated List of Patent Owner's Exhibits dated Jun. 7, 2016, IPR2015-01835, "Dr. Frank Sacks, M.D., Materials Considered".
Ex. 2032 to Updated List of Patent Owner's Exhibits dated Jun. 7, 2016, IPR2015-01835, "Dr. Thomas A. Baillie, Ph.D., D.SC., Materials Considered".
Ex. 2033 to Updated List of Patent Owner's Exhibits dated Jun. 7, 2016, IPR2015-01835, "David Kimball, Ph.D., Materials Considered".
Ex. 2034 to Updated List of Patent Owner's Exhibits dated Jun. 7, 2016, IPR2015-01835, "Malcolm Rowland et al., Clinical Pharmacokinetics: Concepts and Applications, William and Wilkins (1995)" pp. 1-30.
Ex. 2034 to Updated List of Patent Owner's Exhibits dated Jun. 7, 2016, IPR2015-01835, "Malcolm Rowland et al., Clinical Pharmacokinetics: Concepts and Applications, William and Wilkins (1995)" pp. 142-170.
Ex. 2034 to Updated List of Patent Owner's Exhibits dated Jun. 7, 2016, IPR2015-01835, "Malcolm Rowland et al., Clinical Pharmacokinetics: Concepts and Applications, William and Wilkins (1995)" pp. 171-198.
Ex. 2034 to Updated List of Patent Owner's Exhibits dated Jun. 7, 2016, IPR2015-01835, "Malcolm Rowland et al., Clinical Pharmacokinetics: Concepts and Applications, William and Wilkins (1995)" pp. 199-229.
Ex. 2034 to Updated List of Patent Owner's Exhibits dated Jun. 7, 2016, IPR2015-01835, "Malcolm Rowland et al., Clinical Pharmacokinetics: Concepts and Applications, William and Wilkins (1995)" pp. 31-62.
Ex. 2034 to Updated List of Patent Owner's Exhibits dated Jun. 7, 2016, IPR2015-01835, "Malcolm Rowland et al., Clinical Pharmacokinetics: Concepts and Applications, William and Wilkins (1995)" pp. 63-141.
Ex. 2035 to Updated List of Patent Owner's Exhibits dated Jun. 7, 2016, IPR2015-01835, "Sharon A. Huang et al., Phosphodiesterase-5 (PDE5) Inhibitors in the Management of Erectile Dysfunction, P T, vol. 38, No. 7, pp. 407-419 (Jul. 2013)".
Ex. 2036 to Updated List of Patent Owner's Exhibits dated Jun. 7, 2016, IPR2015-01835, "Heinz Lüllmann et al, Lipidosis Induced by Amphiphillic Cationic Drugs, Biochem. Pharmacol., vol. 27, pp. 1103-1108 (1978)".
Ex. 2037 to Updated List of Patent Owner's Exhibits dated Jun. 7, 2016, IPR2015-01835, "Jan-Peter H. T. M. Ploemen et al., Use of physiochemical calculation of pKa and CLogP to predict phospholipidosis-inducing potential: A case study with structurally related piperazines, Exp. Toxic Pathol., vol. 55, pp. 347-355 (2004)".
Ex. 2038 to Updated List of Patent Owner's Exhibits dated Jun. 7, 2016, IPR2015-01835, "Andrea Cavalli et al., Toward a pharmacophore for drugs inducing the long QT syndrome: insights from a CoMFA study of HERG K(+) channel blockers, J. Med. Chem., vol. 45, pp. 3844-3853 (2002)".
Ex. 2039 to Updated List of Patent Owner's Exhibits dated Jun. 7, 2016, IPR2015-01835, "John S. Walsh et al., The Metabolic Activation of Abacavir by Human Liver Cytosol and Expressed Human Alcohol Dehydrogenase Isozymes, Chem. Biol. Interact., vol. 142, pp. 135-154 (2002)".
Ex. 2040 to Updated List of Patent Owner's Exhibits dated Jun. 7, 2016, IPR2015-01835, "Jean F. Le Bigot et al., Metabolism of Ketotifen by Human Liver Microsomes, Drug Metab. Dispos., vol. 11, pp. 585-589 (1983)".
Ex. 2041 to Updated List of Patent Owner's Exhibits dated Jun. 7, 2016, IPR2015-01835, "Press Release, Aegerion Pharmaceuticals, FDA Advisory Committee Recommends Approval of Lomitapide for Treatment of Homozygous Familial Hypercholesterolemia (HoFH) (Oct. 17, 2012)".
Ex. 2042 to Updated List of Patent Owner's Exhibits dated Jun. 7, 2016, IPR2015-01835, "Pharmaceutical Product Development, Inc., Annual Report (Form 10-K) (Dec. 31, 2005)".
Ex. 2043 to Updated List of Patent Owner's Exhibits dated Jun. 7, 2016, IPR2015-01835, "Frank M. Sacks et al., Severe Hypertriglyceridemia With Pancreatitis: Thirteen Years' Treatment With Lomitapide, JAMA Intern. Med., vol. 174, No. 3 (Mar. 2014)".
Ex. 2044 to Updated List of Patent Owner's Exhibits dated Jun. 7, 2016, IPR2015-01835, Internet Archive WayBack, Machine Error Message (Jun. 6, 2016).
Ex. 2045 to Updated List of Patent Owner's Exhibits dated Jun. 7, 2016, IPR2015-01835, Internet Archive WayBack Machine, PPD Analyst/Investor Day: Dapoxetine.
Ex. 2046 to Updated List of Patent Owner's Exhibits dated Jun. 7, 2016, IPR2015-01835, Internet Archive WayBack Machine, PPD Analyst/Investor Day: DP4 Inhibitor.
Ex. 2050 to Updated List of Patent Owner's Exhibits dated Jun. 7, 2016, IPR2015-01835, "Patent Owner's Motion to Amend Under 37 C.F.R. § 42.121."
Ex. 2051 to Updated List of Patent Owner's Exhibits dated Jun. 7, 2016, IPR2015-01835, "Marjel van Dam et al., Efficacy and Safety of Implitapide (Bay 13-9952), a Microsomal Triglyceride Transfer Protein Inhibitor, in Patients with Primary Hypercholesterlemia, Stein Phase I Study (2001)".
Ex. 2052 to Updated List of Patent Owner's Exhibits dated Jun. 7, 2016, IPR2015-01835, "Daru Sharp et al., Cloning and gene defects in microsomal triglyceride transfer protein associated with abetalipoproteinaemia, Nature 365, 65-69 (Sep. 2, 1993)".
Ex. 2053 to Updated List of Patent Owner's Exhibits dated Jun. 7, 2016, IPR2015-01835, "Marc A. Pfeffer et al., Safety and tolerability of pravastatin in long-term clinical trials". Prospective Pravastatin Pooling (PPP) Project, CIRC. (May 21, 2002).
Ex. 2054 to Updated List of Patent Owner's Exhibits dated Jun. 7, 2016, IPR2015-01835, "J. D. Adams et al., Studies on the biotransformation of ketamine. I—Identification of metabolites produced in vitro from rat liver microsomal preparations, Bio. Mass Spectrom., vol. 8, No. 8 (Aug. 1981)".
Ex. 2055 to Updated List of Patent Owner's Exhibits dated Jun. 7, 2016, IPR2015-01835, "Richard E. Gregg, M.D., curriculam vitae".
Ex. 2056 to Updated List of Patent Owner's Exhibits dated Jun. 7, 2016, IPR2015-01835, "John R. Wetterau et al., Absence of Microsomal Triglyceride Transfer Protein in Individuals with Abetalipoproteinemia, Science, vol. 258 (Nov. 6, 1992)".
Ex. 2057 to Updated List of Patent Owner's Exhibits dated Jun. 7, 2016, IPR2015-01835, "Bristol Meyers Squibb, Clinical Study Report, The Effects of Chronic Dosing of BMS-201038 on Hepatic Fat Accumulation and Reversibility as Assessed by Nuclear Magnetic Resonance Spectroscopy (NMRS), (Jan. 2002) (filed under seal)".

(56) References Cited

OTHER PUBLICATIONS

Ex. 2058 to Updated List of Patent Owner's Exhibits dated Jun. 7, 2016, IPR2015-01835, "Bristol Meyers Squibb, BMS-201038 Investigator Brochure General Addendum (Oct. 1997)".
Ex. 2059 to Updated List of Patent Owner's Exhibits dated Jun. 7, 2016, IPR2015-01835, Adrien Albert, Xenobiosis: Food, Drugs and Poisons in the Human Body, Chapman & Hall (1987).
Ex. 2060 to Updated List of Patent Owner's Exhibits dated Jun. 7, 2016, IPR2015-01835, "Goodman, et. al., Goodman & Gilman's The Pharmacological Basis of Therapeutics, (Macmillan Publishing Compnay) (1985)".
Ex. 2061 to Updated List of Patent Owner's Exhibits dated Jun. 7, 2016, IPR2015-01835, "Han van de Waterbeemd et al., ADMET in Silico Modelling: Towards Prediction Paradise?, Nat. Rev. Drug. Discov., vol. 2, No. 3, pp. 192-204 (2003)".
Ex. 2062 to Updated List of Patent Owner's Exhibits dated Jun. 7, 2016, IPR2015-01835, "35 FDA-Approved Prescription Drugs Later Pulled from the Market (Jan. 30, 2014, 1:09 PM), http://prescriptiondrugs.procon.org/view.resource.php?resourceID=005528".
Ex. 2063 to Updated List of Patent Owner's Exhibits dated Jun. 7, 2016, IPR2015-01835, "William H. Halliwell, Cationic Amphiphilic Drug-Induced Phospholipidosis, Toxicol. Pathol., vol. 25, pp. 53-60 (1997)".
Ex. 2064 to Updated List of Patent Owner's Exhibits dated Jun. 7, 2016, IPR2015-01835, "Holger Fischer et. al, CAFCA: A Novel Tool for the Calculation of Amphiphilic Properties of Charged Drug Molecules, CHIMIA, vol. 54, No. 11, pp. 640-645 (2000)".
Ex. 2065 to Updated List of Patent Owner's Exhibits dated Jun. 7, 2016, IPR2015-01835, "R. Preston Mason, et. al., Reevaluating Equilibrium and Kinetic Binding Parameters for Lipophilic Drugs Based on a Structural Model for Drug Interaction with Biological Membranes, J. Med. Chem., vol. 34, No. 2, pp. 869-877 (Mar. 1991)".
Ex. 2066 to Updated List of Patent Owner's Exhibits dated Jun. 7, 2016, IPR2015-01835, "Martin Tristani-Firouzi, et. al., Molecular Biology of K+ Channels and Their Role in Cardiac Arrhythmias, Am. J. Med., vol. 110, pp. 50-59 (2001)".
Ex. 2067 to Updated List of Patent Owner's Exhibits dated Jun. 7, 2016, IPR2015-01835, "Mark E. Curran, et. al, A Molecular Basis for Cardiac Arrhythmia: HERG Mutations Cause Long QT Syndrome, Cell, vol. 80, pp. 795-803 (1995)".
Ex. 2068 to Updated List of Patent Owner's Exhibits dated Jun. 7, 2016, IPR2015-01835, "Bernadr Fermini et al., Pre-Clinical Assessment of Drug-Induced QT Interval Prolongation, Current Issues and Impact on Drug Discovery, Annu. Rep. Med. Chem., vol. 39, pp. 323-333 (2004)".
Ex. 2069 to Updated List of Patent Owner's Exhibits dated Jun. 7, 2016, IPR2015-01835, "William Crumb et al., QT Interval Prolongation by Non-cardiovascular Drugs: Issues and Solutions for Novel Drug Development, Pharm. Sci. Technol. Today, vol. 2, No. 7, pp. 270-280 (1999)".
Ex. 2070 to Updated List of Patent Owner's Exhibits dated Jun. 7, 2016, IPR2015-01835, "Man-Wai Lo, et. al., Pharmacokinetics of losartan, an angiotensin II receptor antagonist, and its active metabolite EXP3174 in humans, Clin. Pharmacol. Ther., vol. 58, No. 6, pp. 641-649 (1995)".
Ex. 2071 to Updated List of Patent Owner's Exhibits dated Jun. 7, 2016, IPR2015-01835, "Stephen J. Cutler et al., Wilson and Grisvold's Textbook of Organic Medicinal and Pharmaceutical Chemistry, 65-66 (11th ed. 2004)".
Ex. 2072 to Updated List of Patent Owner's Exhibits dated Jun. 7, 2016, IPR2015-01835, "Christopher P. Cannon et al., Intensive versus Moderate Lipid Lowering with Statins after Acute Coronary Syndromes, N. Eng. J. Med., vol. 350, No. 15 (Apr. 8, 2004)".
Ex. 2073 to Updated List of Patent Owner's Exhibits dated Jun. 7, 2016, IPR2015-01835, "List of Prior Art Reviewed by Frank Sacks, M.D. for Motion to Amend".
Ex. 2074 to Updated List of Patent Owner's Exhibits dated Jun. 7, 2016, IPR2015-01835, "H. Mabuchi et al., Causes of death in patients with familial hypercholesterolemia, Atherosclerosis, vol. 61, No. 1, pp. 1-6 (1986)".
Ex. 2075 to Updated List of Patent Owner's Exhibits dated Jun. 7, 2016, IPR2015-01835, "Aegerion Pharmaceuticals, Inc., U.S. Securities and Exchange Commission (Form 10-K) (Mar. 15, 2016)" pp. 1-18.
Ex. 2075 to Updated List of Patent Owner's Exhibits dated Jun. 7, 2016, IPR2015-01835, "Aegerion Pharmaceuticals, Inc., U.S. Securities and Exchange Commission (Form 10-K) (Mar. 15, 2016)" pp. 106-130.
Ex. 2075 to Updated List of Patent Owner's Exhibits dated Jun. 7, 2016, IPR2015-01835, "Aegerion Pharmaceuticals, Inc., U.S. Securities and Exchange Commission (Form 10-K) (Mar. 15, 2016)" pp. 131-151.
Ex. 2075 to Updated List of Patent Owner's Exhibits dated Jun. 7, 2016, IPR2015-01835, "Aegerion Pharmaceuticals, Inc., U.S. Securities and Exchange Commission (Form 10-K) (Mar. 15, 2016)" pp. 152-174.
Ex. 2075 to Updated List of Patent Owner's Exhibits dated Jun. 7, 2016, IPR2015-01835, "Aegerion Pharmaceuticals, Inc., U.S. Securities and Exchange Commission (Form 10-K) (Mar. 15, 2016)" pp. 19-34.
Ex. 2075 to Updated List of Patent Owner's Exhibits dated Jun. 7, 2016, IPR2015-01835, "Aegerion Pharmaceuticals, Inc., U.S. Securities and Exchange Commission (Form 10-K) (Mar. 15, 2016)" pp. 35-51.
Ex. 2075 to Updated List of Patent Owner's Exhibits dated Jun. 7, 2016, IPR2015-01835, "Aegerion Pharmaceuticals, Inc., U.S. Securities and Exchange Commission (Form 10-K) (Mar. 15, 2016)" pp. 52-67.
Ex. 2075 to Updated List of Patent Owner's Exhibits dated Jun. 7, 2016, IPR2015-01835, "Aegerion Pharmaceuticals, Inc., U.S. Securities and Exchange Commission (Form 10-K) (Mar. 15, 2016)" pp. 68-85.
Ex. 2075 to Updated List of Patent Owner's Exhibits dated Jun. 7, 2016, IPR2015-01835, "Aegerion Pharmaceuticals, Inc., U.S. Securities and Exchange Commission (Form 10-K) (Mar. 15, 2016)" pp. 86-105.
Ex. 2076 to Updated List of Patent Owner's Exhibits dated Jun. 7, 2016, IPR2015-01835, "Aegerion Pharmaceuticals, Inc., U.S. Securities and Exchange Commission (Form 10-Q) (May 16, 2016)", pp. 1-25.
Ex. 2076 to Updated List of Patent Owner's Exhibits dated Jun. 7, 2016, IPR2015-01835, "Aegerion Pharmaceuticals, Inc., U.S. Securities and Exchange Commission (Form 10-Q) (May 16, 2016)", pp. 26-42.
Ex. 2076 to Updated List of Patent Owner's Exhibits dated Jun. 7, 2016, IPR2015-01835, "Aegerion Pharmaceuticals, Inc., U.S. Securities and Exchange Commission (Form 10-Q) (May 16, 2016)", pp. 43-59.
Ex. 2076 to Updated List of Patent Owner's Exhibits dated Jun. 7, 2016, IPR2015-01835, "Aegerion Pharmaceuticals, Inc., U.S. Securities and Exchange Commission (Form 10-Q) (May 16, 2016)", pp. 60-74.
Ex. 2076 to Updated List of Patent Owner's Exhibits dated Jun. 7, 2016, IPR2015-01835, "Aegerion Pharmaceuticals, Inc., U.S. Securities and Exchange Commission (Form 10-Q) (May 16, 2016)", pp. 75-91.
Ex. 2076 to Updated List of Patent Owner's Exhibits dated Jun. 7, 2016, IPR2015-01835, "Aegerion Pharmaceuticals, Inc., U.S. Securities and Exchange Commission (Form 10-Q) (May 16, 2016)", pp. 92-102.
Ex. 2076 to Updated List of Patent Owner's Exhibits dated Jun. 7, 2016, IPR2015-01835, "Aegerion Pharmaceuticals, Inc., U.S. Securities and Exchange Commission (Form 10-Q) (May 16, 2016)".
Ex. 2077 to Updated List of Patent Owner's Exhibits dated Jun. 7, 2016, IPR2015-01835, Dec. 2002 Final Clinical Trial Protocol Submitted to Institutional Review Board.
Ex. 2078 to Updated List of Patent Owner's Exhibits dated Jun. 7, 2016, IPR2015-01835, "BMS-201038 Investigator Brochure General Addendum CV145-002, Multiple Dose PO (Oct. 1, 1997)".

(56) References Cited

OTHER PUBLICATIONS

Ex. 2079 to Updated List of Patent Owner's Exhibits dated Jun. 7, 2016, IPR2015-01835, "Clinical Study Approval (Mar. 20, 2003)".
Ex. 2080 to Updated List of Patent Owner's Exhibits dated Jun. 7, 2016, IPR2015-01835, "Abbreviated Clinical Study Report for CV145-009 (Jan. 7, 2002)".
Ex. 2081 to Updated List of Patent Owner's Exhibits dated Jun. 7, 2016, IPR2015-01835, "Interim Clinical Study Summary Submitted to the Dorris Duke Charitable Foundation (Oct. 2003) (filed under seal)".
Ex. 2082 to Updated List of Patent Owner's Exhibits dated Jun. 7, 2016, IPR2015-01835, "Memorandum Summarizing Results of Clinical Trial (Feb. 9, 2004) (filed under seal)".
Ex. 2083 to Updated List of Patent Owner's Exhibits dated Jun. 7, 2016, IPR2015-01835, Declaration of Richard E. Gregg.
Ex. 2084 to Updated List of Patent Owner's Exhibits dated Jun. 7, 2016, IPR2015-01835, "Aegerion Pharmaceuticals 2013 Annual Report".
Ex. 2085 to Updated List of Patent Owner's Exhibits dated Jun. 7, 2016, IPR2015-01835, "Marina Cuchel et al., Homozygous familial hypercholesterolaemia: new insights and guidance for clinicians to improve detection and clinicalmanagement. A position paper fromthe Consensus Panel on Familial Hypercholesterolaemia of the European Atherosclerosis Society, Eur. Heart J., 35, at 2146-2157 (2014)".
Ex. 2086 to Updated List of Patent Owner's Exhibits dated Jun. 7, 2016, IPR2015-01835, "Visioli, F., "Microsomoal triglyceride transfer protein inhibitors," Current Opinion in Cardiovascular, Pulmonary & Renal Investigational Drugs 2000 2(3):292-293".
Ex. 2087 to Updated List of Patent Owner's Exhibits dated Jun. 7, 2016, IPR2015-01835, "Williams, S. et al., "Novel microsomal triglyceride transfer protein inhibitors," Expert Opin. Ther. Patents (2003) 13(4): 479-488".
Ex. 2088 to Updated List of Patent Owner's Exhibits dated Jun. 7, 2016, IPR2015-01835, "Funatsu, T. et al. "Atorvastatin Increases Hepatic Fatty Acid Beta-Oxidation in Sucrose-Fed Rats: Comparison with an MTP Inhibitor" European Journal of Pharmacology 455 (2002) 161-167".
Ex. 2089 to Updated List of Patent Owner's Exhibits dated Jun. 7, 2016, IPR2015-01835, "Barclay, L., "Hyperlipidemia", NMT Briefs, 2003, 1-4".
Ex. 2090 to Updated List of Patent Owner's Exhibits dated Jun. 7, 2016, IPR2015-01835, "Evans, M., et al., "Medical Lipid-Regulating Therapy: Current Evidence, Ongoing Trials and Future Developments," Drugs 2004: 64 (11): 1181-1196".
Ex. 2103 to Updated List of Patent Owner's Exhibits dated Jun. 7, 2016, IPR2015-01835, "van Dam, M.J., Dyslipidemia; diagnosis and treatment, Dissertation, UvA-DARE, 2001, 147-157".
Ex. 2104 to Updated List of Patent Owner's Exhibits dated Jun. 7, 2016, IPR2015-01835, "U.S. National Institutes of Health, Implitapide in Patients With Hypertriglyceridemia on Maximal, Concurrent Triglyceride-Lowering Therapy, NIH Clinical Trials. gov, NT0008013, 2004, 1-3".
Ex. 2105 to Updated List of Patent Owner's Exhibits dated Jun. 7, 2016, IPR2015-01835, "U.S. National Institutes of Health, Implitapide in Patients With Homozygous Familial Hypercholesterolemia on Maximal Concurrent Lipid-Lowering Therapy, NIH Clinical Trials.gov, NCT00079846, 2003, 1-3".
Ex. 2106 to Updated List of Patent Owner's Exhibits dated Jun. 7, 2016, IPR2015-01835, "Baddour, L. et al., PPD to Hold Analyst Day on Feb. 5, 2004 (Jan. 15, 2004)".
Ex. 2107 to Updated List of Patent Owner's Exhibits dated Jun. 7, 2016, IPR2015-01835, "Gruetzmann R., et al., "Impiltapide inhibits secretation of apoB-associated lipoproteins by inhibition of the MTP," Eur. Heart J. 2000, 21 (Suppl), Abst 3271, p. 600".
Ex. 2108 to Updated List of Patent Owner's Exhibits dated Jun. 7, 2016, IPR2015-01835, "Bischoff, H., et al., Bay 13-9952 (implitapide): pharmacodynamic effects of a new MTP inhibitor on plasma lipids and adipose tissue in animals, Eur. Heart J. 2000, 21 (Suppl), Abst P3501, p. 636".

Ex. 2109 to Updated List of Patent Owner's Exhibits dated Jun. 7, 2016, IPR2015-01835, "Zaiss, S., et al., 194, Bay 13-9952 (Implitapide), an inhibitor of the MTP, inhibits atherosclerosis and prolongs lifetime in apo-E knockout mice, Eur. Hert J. 2000, 21 (Suppl), Abst 194, p. 16".
Ex. 2110 to Updated List of Patent Owner's Exhibits dated Jun. 7, 2016, IPR2015-01835, "Bayes, M., et al., Gateways to Clinical Trials, Methods Find Exp Clin Pharmacol 2002, 24(1): 37-55".
Ex. 2111 to Updated List of Patent Owner's Exhibits dated Jun. 7, 2016, IPR2015-01835, "Sorbera, L.A., et al., Implitapide, Drugs of the Future, 2000, 25(11): 1138-1144".
Ex. 2123 to Updated List of Patent Owner's Exhibits dated Jun. 7, 2016, IPR2015-01835, "Aguilar-Salinas, C., et al., Efficacy and safety of atorvastatin in hyperlipidemic, type 2 diabetic patients. A 34-week, multicenter, open-label study, Eslevier, Atheroslerosis, 2000, 489-496".
Ex. 2124 to Updated List of Patent Owner's Exhibits dated Jun. 7, 2016, IPR2015-01835, "Capuzzi, D., et al., Niacin Dosing: Relationship to Benefits and Adverse Effect, Current Atherosclerosis Reports, 2000, 2, 64-71".
Ex. 2125 to Updated List of Patent Owner's Exhibits dated Jun. 7, 2016, IPR2015-01835, "Teramoto T. et al.; Effect of large dose of niceritrol (Perycit) on hypercholesterolemia-by administering Gradually Increasing Doses, Hardening of the arteries (1991), 199-208".
Ex. 2126 to Updated List of Patent Owner's Exhibits dated Jun. 7, 2016, IPR2015-01835, "Reference 4 cited in JPA No. 2007-502093, vol. 40, 3389-3397".
Ex. 2127 to Updated List of Patent Owner's Exhibits dated Jun. 7, 2016, IPR2015-01835, "Knopp R., Treatment of Lipid Disorders, New England Journal of Medicine, Aug. 1999,vol. 341:498-511".
Ex. 2128 to Updated List of Patent Owner's Exhibits dated Jun. 7, 2016, IPR2015-01835, "Bays, H. et al., Pharmacotherapy for dyslipidaemia-current therapies and future agents, Expert Opin. Pharmacother. (2003) 4(11), 1901-38".
Ex. 2129 to Updated List of Patent Owner's Exhibits dated Jun. 7, 2016, IPR2015-01835, "Bruckert, E., New lipid-modifying therapies, Expert Opin. Invescig. Drugs (2003) 12(3): 325-335".
Ex. 2130 to Updated List of Patent Owner's Exhibits dated Jun. 7, 2016, IPR2015-01835, "Kastelein, J., What future for combination therapies? Int. J. Clin. Pract. Suppl. Mar. 2003, (134), 45-50".
Ex. 2146 to Updated List of Patent Owner's Exhibits dated Jun. 7, 2016, IPR2015-01835, Microsomal Triglyceride Transfer Protein, 1-6.
Ex. 2147 to Updated List of Patent Owner's Exhibits dated Jun. 7, 2016, IPR2015-01835, "Wetterau, J., et al., Microsomal triglyceride transfer protein, Biochimica et Biophysica Acta 1345 (1997) 136-150".
Ex. 2148 to Updated List of Patent Owner's Exhibits dated Jun. 7, 2016, IPR2015-01835, "Thomas, L., Alleviation of MTP inhibitor-induced hepatic steatosis in hyperlipidemic fa/fa rats by fenofibrate, Department of Metabolic Diseases and Dept. of Chemical Research, Boehringer Ingelheim, 1 page".
Ex. 2149 to Updated List of Patent Owner's Exhibits dated Jun. 7, 2016, IPR2015-01835, "Wierzbicki, A., New lipid-lowering agents, Expert Opin. Emerging Drugs (2003) 8(2): 365-376".
Ex. 2150 to Updated List of Patent Owner's Exhibits dated Jun. 7, 2016, IPR2015-01835, "Atzel, A., et al., Mechanism of Microsomal Triglyceride Transfer Protein Catalyzed Lipid Transport, Biochemistry 1993, 32, 10444-10450".
Ex. 2151 to Updated List of Patent Owner's Exhibits dated Jun. 7, 2016, IPR2015-01835, "Bakillah, A., et al., Decreased Secretion of ApoB Follows Inhibition of ApoB-MTP Binding by a Novel Antagonist, Biochemistry 2000, 39, 4892-4899".
Ex. 2152 to Updated List of Patent Owner's Exhibits dated Jun. 7, 2016, IPR2015-01835, "Jamil, H., et al., An inhibitor of the microsomal triglyceride transfer protein inhibits apoB secretion from HepG2 cells, Proc. Natl. Acad. Sci. USA, vol. 93, 1996. 11991-11995".
Ex. 2153 to Updated List of Patent Owner's Exhibits dated Jun. 7, 2016, IPR2015-01835, "Liao, W., et al., Blocking microsomal

(56) References Cited

OTHER PUBLICATIONS triglyceride transfer protein interferes with apoB secretion without causing retention or stress in the ER, Journal of Lipid Research, vol. 44, 2003, 978-985".
Ex. 2174 to Updated List of Patent Owner's Exhibits dated Jun. 7, 2016, IPR2015-01835, "Parsons, C.G., et al., Memantine is a clinically well tolerated NMDA receptor antagonist—a review of preclinical data, Neuropharmacology 38 (1999) 735-767".
Ex. 2175 to Updated List of Patent Owner's Exhibits dated Jun. 7, 2016, IPR2015-01835, "Catapano, A.L., Ezetimibe: a selective inhibitor of cholesterol absorption, European Heart Journal Supplements (2001) 3 (Supplement E), E6-E10".
Ex. 2176 to Updated List of Patent Owner's Exhibits dated Jun. 7, 2016, IPR2015-01835, "Capson, T., Synthesis and Evaluation of Ammonium Analogs of Carbocationic Intermediates in Squalene Biosynthesis, Dissertation, Department of Med. Chem., The University of Utah, vol. 4803B of Dissertations Abstracts International, 1987, Abstract".
Ex. 2177 to Updated List of Patent Owner's Exhibits dated Jun. 7, 2016, IPR2015-01835, "Corey, E.J., et al. Application of Unreactive Analogs of Terpenoid Pyrophsphates to Studies of Multistep Biosynthesis, Demonstration That "Presqualene Pyrophosphate" is an Essential Intermediate on the Path to Squalene, Journal. Of the American Chemical Society, 98:5, 1976, 1291-93".
Ex. 2178 to Updated List of Patent Owner's Exhibits dated Jun. 7, 2016, IPR2015-01835, "De Montellano, P., et al., Inhibition of Squalene Synthetase by Farnesyl Pyrophosphate Analogues, Journal of Medicinal Chemistry, 1977, vol. 20, 243-49".
Ex. 2179 to Updated List of Patent Owner's Exhibits dated Jun. 7, 2016, IPR2015-01835, "Earl, J., et al., Ezetimbe, Nature Reviews, vol. 2, 2003, 97".
Ex. 2180 to Updated List of Patent Owner's Exhibits dated Jun. 7, 2016, IPR2015-01835, "National Cholesterol Education Program, Adult Treatment Panel III Report, 2001, 373 pages".
Ex. 2181 to Updated List of Patent Owner's Exhibits dated Jun. 7, 2016, IPR2015-01835, "Farrell, G., Drugs and Steatohepatitis, Seminars in Liver Disease, vol. 22, No. 2, 2002, 185-194".
Ex. 2182 to Updated List of Patent Owner's Exhibits dated Jun. 7, 2016, IPR2015-01835, "Gagne, C., et al., Efficacy and Safety of Ezetimibe Coadministered With Atorvastatin or Simvastatin in Patients with Homozygous Familial Hypercholesterolemia, Circulation, 2002; 105:2469-2475".
Ex. 2183 to Updated List of Patent Owner's Exhibits dated Jun. 7, 2016, IPR2015-01835, "Kirkpatrick, P., et al., Market Indicators, Nature, vol. 2, 2003, 98".
Ex. 2184 to Updated List of Patent Owner's Exhibits dated Jun. 7, 2016, IPR2015-01835, "McClard, R., Novel Phosphonylphosphinyl Analogues of Biochemically Interesting Diphosphates, Syntheses and Properties of P—C—P—C Analogues of Isopentenyl Diphosphate and Dimethylally Diphosphate, J. Am. Chem. Soc., 1987, 109, 5544-5".
Ex. 2185 to Updated List of Patent Owner's Exhibits dated Jun. 7, 2016, IPR2015-01835, "Ritter, T., et al., Heterocyclic ring scaffolds as small-molecule cholesterol absorption inhibitors, Org. Biomol. Chem., 2005, 3, 3514-3523".
Ex. 2186 to Updated List of Patent Owner's Exhibits dated Jun. 7, 2016, IPR2015-01835, "Sudhop, T., et al., Cholesterol Absorption Inhibitors for the Treatment of Hypercholesterolaaemia, Drugs, 2002; 62(16), 2333-2347".
Ex. 2261 to Updated List of Patent Owner's Exhibits dated Jun. 7, 2016, IPR2015-01835, "Hussain, M., et al., Multiple functions of microsomal triglyceride transfer protein, Nutrition & Metabolism, 2012, 9:14, 1-16".
Ex. 2262 to Updated List of Patent Owner's Exhibits dated Jun. 7, 2016, IPR2015-01835, "Li. J., et al., Bioorganic & Medicinal Chemistry Letters 16 (2006) 3039-3042".
Ex. 2263 to Updated List of Patent Owner's Exhibits dated Jun. 7, 2016, IPR2015-01835, "Looije, N., et al., Disodium Ascorbyl Phytostanyl Phosphates reduces plasma cholesterol concentration, body weight and abdominal fat gain within a dietary-induced obese mouse model, J Pharm Pharmaceut Sci 8 (3):400-408, 2005".
Ex. 2264 to Updated List of Patent Owner's Exhibits dated Jun. 7, 2016, IPR2015-01835, "Aggarwal, D., et al., JTT-130, a microsomal triglyceride transfer protein inhibitor lowers plasma triglycerides and LDL cholesterol concentrations without increasing hepatic triglycerides in guinea pigs, BMC Cardiovascular Disorders 2005, 5:30, 1-8".
Ex. 2265 to Updated List of Patent Owner's Exhibits dated Jun. 7, 2016, IPR2015-01835, "Samaha, F., et al., Inhibition of microsomal triglyceride transfer protein alone or with ezetimibe in patients with moderate hypercholesterolemia, Nature Clinical Practice, Cardiovascular Medicine, Aug. 2008, vol. 5 No. 8, 497-505".
Ex. 2300 to Updated List of Patent Owner's Exhibits dated Jun. 7, 2016, IPR2015-01835, "Aegerion Pharmaceuticals, Starting Juxtapid (Accessed Jun. 7, 2016) <http://www.juxtapid.com/starting-juxtapid>".
Ex. 2301 to Updated List of Patent Owner's Exhibits dated Jun. 7, 2016, IPR2015-01835, "Aegerion Pharmaceuticals, Dosing and Administration (Accessed Jun. 7, 2016) http://www.juxtapid.com/healthcare-professionals/dosing-and-administration".
Notice of Deposition of Michael Mayersohn, Ph.D. (Paper No. 10), dated Apr. 25, 2016, in IPR2015-01835 (3 pages).
Notice of Deposition of Michael Mayersohn, Ph.D. (Paper No. 10), dated Apr. 25, 2016, in IPR2015-01836 (3 pages).
Notice of Deposition of Randall M. Zusman, M.D. (Paper No. 11), dated Apr. 25, 2016, in IPR2015-01835 (3 pages).
Notice of Deposition of Randall M. Zusman, M.D. (Paper No. 11), dated Apr. 25, 2016, in IPR2015-01836 (3 pages).
Patent Owner's Motion to Amend Under 37 C.F.R. § 42.121 (Paper No. 18), dated Jun. 7, 2016, in IPR2015-01835 (42 pages).
Patent Owner's Motion to Amend Under 37 C.F.R. § 42.121 (Paper No. 18), dated Jun. 7, 2016, in IPR2015-01836 (42 pages).
Patent Owner's Motion to Seal (Paper No. 19), dated Jun. 7, 2016, in IPR2015-01835 (6 pages).
Patent Owner's Motion to Seal (Paper No. 19), dated Jun. 7, 2016, in IPR2015-01836 (6 pages).
Patent Owner's Response (Paper No. 16), dated Jun. 7, 2016, in IPR2015-01835 (74 pages).
Patent Owner's Response (Paper No. 16), dated Jun. 7, 2016, in IPR2015-01836 (74 pages).
PTAB Order [on] Motions for Pro Hac Vice Admission of Nicholas K. Mitrokostas [under] 37 C.F.R. §42.10 (Paper No. 14), entered May 17, 2016, in Consolidated Proceedings IPR2015-01835 and IPR2015-01836 (3 pages).
PTAB Order re: Conduct of the Proceedings under 37 C.F.R. §42.5 (Paper No. 15), entered Jun. 3, 2016, in Consolidated Proceedings IPR2015-01835 and IPR2015-01836 (3 pages).
Stipulated Motion for Entry of Protective Order (Paper No. 17), dated Jun. 7, 2016, in IPR2015-01835 (9 pages).
Stipulated Motion for Entry of Protective Order (Paper No. 17), dated Jun. 7, 2016, in IPR2015-01836 (9 pages).
Updated List of Patent Owner's Exhibits (Paper No. 13), dated May 5, 2016, in IPR2015-01835 (4 pages).
Updated List of Patent Owner's Exhibits (Paper No. 13), dated May 5, 2016, in IPR2015-01836 (4 pages).
Updated List of Patent Owner's Exhibits (Paper No. 20), dated Jun. 7, 2016, in IPR2015-01835 (21 pages).
Updated List of Patent Owner's Exhibits (Paper No. 20), dated Jun. 7, 2016, in IPR2015-01836 (21 pages).
Abell, et al. A simplified method for the estimation of total cholesterol in serum and demonstration of its specificity. J Biol Chem. 1952; 195:357-362.
ADROCA '135 IPR, Exhibit 1001—Certified U.S. Pat. No. 8,618,135 to Rader.
ADROCA '135 IPR, Exhibit 1002—Declaration of Randall M. Zusman, M.D.
ADROCA '135 IPR, Exhibit 1003—Declaration of Michael Mayersohn, Ph.D.
ADROCA '135 IPR, Exhibit 1004—Affidavit of Christopher Butler, Office Manager, Internet Archive, authenticating Internet Archive URLs (Jun. 16, 2015) (attaching as Ex. A: ; PPD News & IR

(56) References Cited

OTHER PUBLICATIONS

Presentations (Apr. 15, 2004) (available at https://web.archive.org/web/20040415065142/http://ppdi.com/PPD_6_12.htm)).
ADROCA '135 IPR, Exhibit 1005—Affidavit of Christopher Butler, Office Manager, Internet Archive, authenticating Internet Archive URLs (Jun. 12, 2015) (attaching as Ex. A: ; PPD News Releases(Feb. 13, 2004) (available at https://web.archive.org/web/20040213233245/http://www.ppdi.com/PPD_U6.
htm?ID=126662); ; PPD News & IR Presentations(Dec. 12, 2003) (available at https://web.archive.org/web/20031212193444/http://ppdi.com/PPD_6_12.htm); ; PPD News & IR Presentations (Jun. 4, 2004) (available at https://web.archive.org/web/20040604203252/http://www.ppdi.com/PPD_6_12.htm)).
ADROCA '135 IPR, Exhibit 1006—Certified U.S. Appl. No. 60/550,915.
ADROCA '135 IPR, Exhibit 1007—U.S. Pat. No. 8,618,135 (highlighting dosing information not present in U.S. Appl. No. 60/550,915).
ADROCA '135 IPR, Exhibit 1008—U.S. Appl. No. 13/046,118.
ADROCA '135 IPR, Exhibit 1009—In re Application of: Rader, U.S. Appl. No. 13/046,118, Amendment and Response to Oct. 2, 2012 Office Action (Mar. 4, 2013).
ADROCA '135 IPR, Exhibit 1010—In re Application of: Rader, U.S. Appl. No. 13/046,118, Declaration of William Sasiela, Ph.D. (Apr. 8, 2010).
ADROCA '135 IPR, Exhibit 1011—In re Application of: Rader, U.S. Appl. No. 13/046,118, Notice of Allowance (May 10, 2013).
ADROCA '135 IPR, Exhibit 1012—In re Application of: Rader, U.S. Appl. No. 13/046,118, Notice of Allowance (Sep. 3, 2013).
ADROCA '135 IPR, Exhibit 1013—Bayer/PPD Implitapide Development Follows Zetia Model As Statin Add-On, 66 The Pink Sheet 17 (Feb. 16, 2004).
ADROCA '135 IPR, Exhibit 1014—Evan Stein, CEO & President, MRL Int'l (Division of PPD), Presentation Given at PPD's Analyst Day, Microsomal Triglygeride [sic] Transfer Protein (MTP) Inhibitor (implitapide) program (Feb. 5, 2004).
ADROCA '135 IPR, Exhibit 1015—George Chang et al., Microsomal triglyceride transfer protein (MTP) inhibitors: Discovery of clinically active inhibitors using high-throughput screening and parallel synthesis paradigms, 5 Current Opinion in Drug Discovery & Dev. 562 (2002).
ADROCA '135 IPR, Exhibit 1016—Charles E. Chandler et al., CP-346086: an MTP inhibitor that lowers plasma cholesterol and triglycerides in experimental animals and in humans, 44 J. of Lipid Res. 1887 (2003).
ADROCA '135 IPR, Exhibit 1017—FDA approves Zetia-first new class to treat cholesterol since statins introduced, drugs.com (Oct. 28, 2002), http://www.drugs.com/news/fda-approves-zetia-first-new-class-cholesterol-since-statins-introduced-3164.html (last visited Jul. 22, 2015).
ADROCA '135 IPR, Exhibit 1018—John R. Wetterau et al., An MTP Inhibitor That Normalizes Atherogenic Lipoprotein Levels in WHHL Rabbits, 282 Sci. 751 (1998).
ADROCA '135 IPR, Exhibit 1019—U.S. Pat. No. 5,712,279 to Biller et al.
ADROCA '135 IPR, Exhibit 1020—Evan Stein, Opposition Against European Patent No. 1 725 234 B9 (filed Aug. 21, 2013).
ADROCA '135 IPR, Exhibit 1021—Thompson PDR, Physicians' Desk Reference 506-09, 1101-06, 1813-21, 2036-41, 2126-31, 2547-51, 2729-31, 2865-68 (57th ed. 2003) (excerpting product information for Tricor®, Pravachol®, Advicor®, Niaspan®, Mevacor®, Zocor®, Lipitor®, Colestid®, and Lescol®).
ADROCA '135 IPR, Exhibit 1022—Thompson PDR, Physicians' Desk Reference 2118-23, 3085-89 (58th ed. 2004) (excerpting product information for Zetia®).
ADROCA '135 IPR, Exhibit 1023—U.S. Food & Drug Ass'n, Estimating the Maximum Safe Starting Dose in Initial Clinical Trials for Therapeutics in Adult Healthy Volunteers: Guidance for Industry (2005).
ADROCA '135 IPR, Exhibit 1024—Prices and coupons for 30 capsules of Juxtapid 5mg, 10mg, 20mg, 30mg, 40mg and 60mg (brand), goodrx.com, http://www.goodrx.com/juxtapid (last visited Jul. 16, 2015).
ADROCA '135 IPR, Exhibit 1025—Dan Mangan, 'Fast Money' faux pas: Firm draws FDA warning, DOJ subpoena, cnbc.com (Jan. 13, 2014), http://www.cnbc.com/id/101327742 (last visited Jul. 22, 2015).
ADROCA '135 IPR, Exhibit 1026—Malcolm Rowland & Thomas N. Tozer, Clinical Pharmacokinetics: Concepts and Applications 57 (3d ed. 1995).
ADROCA '135 IPR, Exhibit 1027—Curriculum Vitae of Randall M. Zusman, M.D.
ADROCA '135 IPR, Exhibit 1028—Documents considered by Randall M. Zusman, M.D.
ADROCA '135 IPR, Exhibit 1029—Curriculum Vitae of Michael Mayersohn, Ph.D.
ADROCA '135 IPR, Exhibit 1030—Documents considered by Michael Mayersohn, Ph.D.
ADROCA '135 IPR, Exhibit 1031—Third Report of the National Cholesterol Education Program (NCEP) Expert Panel on Detection, Evaluation and Treatment of High Blood Cholesterol in Adults (Adult Treatment Panel III) Final Report, 106 Circulation 3143 (2002).
ADROCA '135 IPR, Exhibit 1032—Michael Mayersohn, Principles and Applications of Pharmacokinetics, in Medical Toxicology 282 (Richard C. Dart ed., 3d ed. 2004).
ADROCA '135 IPR, Exhibit 1033—Masashi Shiomi & Takashi Ito, MTP inhibitor decreases plasma cholesterol levels in LDL receptor-deficient WHHL rabbits by lowering the VLDL secretion, 431 Eur. J. of Pharmacology 127 (2001).
ADROCA '135 IPR, Exhibit 1034—Declaration of Jeffery A. Marx.
ADROCA '135 IPR, Exhibit 1035—Press Release, Cigna Corp., Cigna Announces Appearance at CIBC Healthcare Conference (Nov. 7, 2003), http://newsroom.cigna.com/article_display.cfm?article_id=236.
ADROCA '135 IPR, Exhibit 1036—Press Release, Gilead Scis., Gilead Sciences to Present at the 7th Annual Lehman Brothers Global Healthcare Conference on Friday, Mar. 5; Webcast Available Through Gilead Corporate Website (Mar. 4, 2004), ; http://gilead.com/news/press-releases/2004/3/gilead-sciences-to-present-at-the-7th-annual-lehman-brothers-global-healthcare-conference-on-friday-march-5th-webcast-available-through-gilead-corporate-website?mode=print.
ADROCA '135 IPR, Exhibit 1037—Press Release, PR Newswire, Dot Hill to Present at Robert W. Baird 2004 Growth Stock Conference (May 4, 2004), http://www.prnewswire.com/news-releases/dot-hill-to-present-at-robert-w-baird-2004-growth-stock-conference-73777807.html.
ADROCA '135 IPR, Exhibit 1038—Margaret A. McDowell et al., Anthropometric Reference Data for Children and Adults: U.S. Population, 1999-2002, CDC Advance Data From Vital & Health Stats. No. 361 (2005).
ADROCA '135 IPR, Exhibit 1039—In re Application of: Rader, U.S. Appl. No. 13/046,118, Amendment (Sep. 25, 2013).
ADROCA '135 IPR, Exhibit 1040—In re Application of: Rader, U.S. Appl. No. 13/046,118, Supplemental Information Disclosure Statement (Sep. 25, 2013).
ADROCA '135 IPR, Exhibit 1041—In re Application of: Rader, U.S. Appl. No. 13/046,118, Notice of Allowance (Oct. 29, 2013).
ADROCA '268 IPR, Exhibit 1001—Certified U.S. Pat. No. 7,932,268 to Rader.
ADROCA '268 IPR, Exhibit 1002—Declaration of Randall M. Zusman, M.D.
ADROCA '268 IPR, Exhibit 1003—Declaration of Michael Mayersohn, Ph.D.
ADROCA '268 IPR, Exhibit 1004—Affidavit of Christopher Butler, Office Manager, Internet Archive, authenticating Internet Archive URLs (Jun. 16, 2015) (attaching as Ex. A: ; PPD News & IR Presentations (Apr. 15, 2004) (available at https://web.archive.org/web/20040415065142/http://ppdi.com/PPD_6_12.htm)).
ADROCA '268 IPR, Exhibit 1005—Affidavit of Christopher Butler, Office Manager, Internet Archive, authenticating Internet Archive

(56) References Cited

OTHER PUBLICATIONS

URLs (Jun. 12, 2015) (attaching as Ex. A: PPD News Releases(Feb. 13, 2004) (available at https://web.archive.org/web/20040213233245/http://www.ppdi.com/PPD_U6.htm?ID=126662); ; PPD News & IR Presentations(Dec. 12, 2003) (available at https://web.archive.org/web/20031212193444/http://ppdi.com/PPD_6_12.htm); ; PPD News & IR Presentations (Jun. 4, 2004) (available at https://web.archive.org/web/20040604203252/http://www.ppdi.com/PPD_6_12.htm)).
ADROCA '268 IPR, Exhibit 1006—Certified U.S. Appl. No. 60/550,915.
ADROCA '268 IPR, Exhibit 1007—U.S. Pat. No. 7,932,268 (highlighting dosing information not present in U.S. Appl. No. 60/550,915).
ADROCA '268 IPR, Exhibit 1008—U.S. Appl. No. 10/591,923.
ADROCA '268 IPR, Exhibit 1009—In re Application of: Rader, U.S. Appl. No. 10/591,923, Response to Oct. 21, 2009 Office Action (Apr. 14, 2010).
ADROCA '268 IPR, Exhibit 1010—In re Application of: Rader, U.S. Appl. No. 10/591,923, Declaration of William Sasiela, Ph.D. (Apr. 8, 2010).
ADROCA '268 IPR, Exhibit 1011—In re Application of: Rader, U.S. Appl. No. 10/591,923, Response to Jul. 26, 2010 Office Action (Sep. 13, 2010).
ADROCA '268 IPR, Exhibit 1012—In re Application of: Rader, U.S. Appl. No. 10/591,923, Notice of Allowance (Jan. 25, 2011).
ADROCA '268 IPR, Exhibit 1013—Bayer/PPD Implitapide Development Follows Zetia Model As Statin Add-On, 66 The Pink Sheet 17 (Feb. 16, 2004).
ADROCA '268 IPR, Exhibit 1014—Evan Stein, CEO & President, MRL Int'l (Division of PPD), Presentation Given at PPD's Analyst Day, Microsomal Triglygeride [sic] Transfer Protein (MTP) Inhibitor (implitapide) program (Feb. 5, 2004).
ADROCA '268 IPR, Exhibit 1015—George Chang et al., Microsomal triglyceride transfer protein (MTP) inhibitors: Discovery of clinically active inhibitors using high-throughput screening and parallel synthesis paradigms, 5 Current Opinion in Drug Discovery & Dev. 562 (2002).
ADROCA '268 IPR, Exhibit 1016—Charles E. Chandler et al., CP-346086: an MTP inhibitor that lowers plasma cholesterol and triglycerides in experimental animals and in humans, 44 J. of Lipid Res. 1887 (2003).
ADROCA '268 IPR, Exhibit 1017—FDA approves Zetia—first new class to treat cholesterol since statins introduced, drugs.com (Oct. 28, 2002), http://www.drugs.com/news/fda-approves-zetia-first-new-class-cholesterol-since-statins-introduced-3164.html (last visited Jul. 22, 2015).
ADROCA '268 IPR, Exhibit 1018—John R. Wetterau et al., An MTP Inhibitor That Normalizes Atherogenic Lipoprotein Levels in WHHL Rabbits, 282 Sci. 751 (1998).
ADROCA '268 IPR, Exhibit 1019—U.S. Pat. No. 5,712,279 to Biller et al.
ADROCA '268 IPR, Exhibit 1020—Evan Stein, Opposition Against European Patent No. 1 725 234 B9 (filed Aug. 21, 2013).
ADROCA '268 IPR, Exhibit 1021—Thompson PDR, Physicians' Desk Reference 506-09, 1101-06, 1813-21, 2036-41, 2126-31, 2547-51, 2729-31, 2865-68 (57th ed. 2003) (excerpting product information for Tricor®, Pravachol®, Advicor®, Niaspan®, Mevacor®, Zocor®, Lipitor®, Colestid®, and Lescol®).
ADROCA '268 IPR, Exhibit 1022—Thompson PDR, Physicians' Desk Reference 2118-23, 3085-89 (58th ed. 2004) (excerpting product information for Zetia®).
ADROCA '268 IPR, Exhibit 1023—U.S. Food & Drug Ass'n, Estimating the Maximum Safe Starting Dose in Initial Clinical Trials for Therapeutics in Adult Healthy Volunteers: Guidance for Industry (2005).
ADROCA '268 IPR, Exhibit 1024—Prices and coupons for 30 capsules of Juxtapid 5mg, 10mg, 20mg, 30mg, 40mg and 60mg (brand), goodrx.com, http://www.goodrx.com/juxtapid (last visited Jul. 16, 2015).
ADROCA '268 IPR, Exhibit 1025—Dan Mangan, 'Fast Money' faux pas: Firm draws FDA warning, DOJ subpoena, cnbc.com (Jan. 13, 2014), http://www.cnbc.com/id/101327742 (last visited Jul. 22, 2015).
ADROCA '268 IPR, Exhibit 1026—Malcolm Rowland & Thomas N. Tozer, Clinical Pharmacokinetics: Concepts and Applications 57 (3d ed. 1995).
ADROCA '268 IPR, Exhibit 1027—Curriculum Vitae of Randall M. Zusman, M.D.
ADROCA '268 IPR, Exhibit 1028—Documents considered by Randall M. Zusman, M.D.
ADROCA '268 IPR, Exhibit 1029—Curriculum Vitae of Michael Mayersohn, Ph.D.
ADROCA '268 IPR, Exhibit 1030—Documents considered by Michael Mayersohn, Ph.D.
ADROCA '268 IPR, Exhibit 1031—Third Report of the National Cholesterol Education Program (NCEP) Expert Panel on Detection, Evaluation and Treatment of High Blood Cholesterol in Adults (Adult Treatment Panel III) Final Report, 106 Circulation 3143 (2002).
ADROCA '268 IPR, Exhibit 1032—Michael Mayersohn, Principles and Applications of Pharmacokinetics, in Medical Toxicology 282 (Richard C. Dart ed., 3d ed. 2004).
ADROCA '268 IPR, Exhibit 1033—Masashi Shiomi & Takashi Ito, MTP inhibitor decreases plasma cholesterol levels in LDL receptor-deficient WHHL rabbits by lowering the VLDL secretion, 431 Eur. J. of Pharmacology 127 (2001).
ADROCA '268 IPR, Exhibit 1034—Declaration of Jeffery A. Marx.
ADROCA '268 IPR, Exhibit 1035—Press Release, Cigna Corp., Cigna Announces Appearance at CIBC Healthcare Conference (Nov. 7, 2003), http://newsroom.cigna.com/article_display.cfm?article_id=236.
ADROCA '268 IPR, Exhibit 1036—Press Release, Gilead Scis., Gilead Sciences to Present at the 7th Annual Lehman Brothers Global Healthcare Conference on Friday, Mar. 5; Webcast Available Through Gilead Corporate Website (Mar. 4, 2004), http://gilead.com/news/press-releases/2004/3/gilead-sciences-to-present-at-the-7th-annual-lehman-brothers-global-healthcare-conference-on-friday-march-5th-webcast-available-through-gilead-corporate-website?mode=print.
ADROCA '268 IPR, Exhibit 1037—Press Release, PR Newswire, Dot Hill to Present at Robert W. Baird 2004 Growth Stock Conference (May 4, 2004), http://www.prnewswire.com/news-releases/dot-hill-to-present-at-robert-w-baird-2004-growth-stock-conference-73777807.html.
ADROCA '268 IPR, Exhibit 1038—Margaret A. McDowell et al., Anthropometric Reference Data for Children and Adults: U.S. Population, 1999-2002, CDC Advance Data From Vital & Health Stats. No. 361 (2005).
Aggarwal, et al; BMC Cardiovasc. Disord. 27;5(1):30 (2005).
Aguilar-Salinas et al., "Efficacy and Safety of Atorvastatin in Hyperlipidemic, Type 2 Diabetic Patients. A 34-Week, Multicenter, Open-Label Study," *Atherosclerosis*, 152:489-496 (2000).
Allain, et al. Enzymatic determination of total serum cholesterol. Clin Chem. 1974;20:470-475.
Anonymous, 'Bayer/PPD Implitapide Development Follows Zetia Model as Statin Add-on,' The Pink Sheet, Feb. 16, 2004 (Feb. 16, 2004), 66(7):17-18.
Anonymous, 'Implitapide in Patients with Homozygous Familial Hypercholesterolemia (HoFH) on Maximal Concurrent Lipid-Lowering Therapy,' Excerpt from ClinicalTrials.gov, CTG Identifier #NCT00079846, Mar. 17, 2004 (Mar. 17, 2004), NIH (Pub), pp. 1-3.
Atzel A et al., 'Mechanism of Microsomal Triglyceride Transfer Protein Catalyzed Lipid Transport,' Biochemistry, Oct. 5, 1993 (Oct. 5, 1993), 32(39):10444-50.
Baddour L, 'PPD to Hold Analyst Day on Feb. 5, 2004,' PPD News Releases, Jan. 15, 2004 (Jan. 15, 2004), Pharmaceutical Product Development, LLC, Wilmington, DE, USA (Pub), p. 1, www.ppdi.com <http://www.ppdi.com>.
Bakillah A et al., 'Decreased Secretion of ApoB Follows Inhibition of ApoB—MTP Binding by a Novel Antagonist,' Biochemistry, Apr. 25, 2000 (Apr. 25, 2000), 39(16):4892-9.

(56) References Cited

OTHER PUBLICATIONS

Barclay L, 'New Medical Therapies. Hyperlipidemia,' NMT Briefs, Thompson CenterWatch, 2003 (2003), Thompson, Boston, MA, USA (Pub), pp. 1-2.

Bayes M et al., 'Gateways to Clinical Trials,' Methods Find Exp Clin Pharmacol, Sep. 2002 (Sep. 2002), 24(7):431-55.

Bays H and Stein EA, 'Pharmacotherapy for Dyslipidaemia—Current Therapies and Future Agents,' Expert Opin Pharmacother, Nov. 2003 (Nov. 2003), 4(11):1901-38.

Biller SA, 'Isoprenoid (Phosphinylmethyl)phosphonates as Inhibitors of Squalene Synthetase,' J Med Chem, Oct. 1988 (Oct. 1988), 31(10):1869-71.

Bischoff H et al., 'BAY 13-9952 (Implitapide): Pharmacodynamic Effects of a New Microsomal Triglyceride Transfer Protein (MTP) Inhibitor on Plasma Lipids and Adipose Tissue in Animals,' Eur Heart J 2000, Aug. 1, 2000 (Aug. 1, 2000), 21(Abstract Suppl):636 (Abstract# P3501).

Bruckert, "New Lipid-Modifying Therapies", Expert Opin. Investig. Drugs, (2003)12(3):325-35.

Capson, (PhD dissertation, Jun. 1987, Dept. Med. Chem. U. of Utah, Abstratct).

Capuzzi et al., "Niacin Dosing: Relationship to Benefits and Adverse Effects," *Current Atherosclerosis Reports*, 2:64-71 (2000).

Catapano AL, 'Ezetimibe: A Selective Inhibitor of Cholesterol Absorption,' Eur Heart J Suppl 2001, Jun. 2001 (Jun. 2001), 3 (Suppl E):E6-E10.

Chandler, et al., J. Lipid. Res. 44(10):1887-901 (2003).

Chang G et al., 'Microsomal Triglyceride Transfer Protein (MTP) Inhibitors: Discovery of Clinically Active Inhibitors Using High-Throughput Screening and Parallel Synthesis Paradigms,' Curr Opin Drug Discov Devel, Jul. 2002 (Jul. 2002), 5(4):562-70.

Corey EJ and Volante RP, 'Application of Unreactive Analogs of Terpenoid Pyrophosphates to Studies of Multistep Biosynthesis. Demonstration That "Presqualene Pyrophosphate" Is an Essential Intermediate on the Path to Squalene,' J Amer Chem Soc, Mar. 1, 1976 (Mar. 1, 1976), 98(5):1291-3.

Cuchel M et al., 'Inhibition of Microsomal Triglyceride Transfer Protein in Familial Hypercholesterolemia,' N Engl J Med, Jan. 11, 2007 (Jan. 11, 2007), 356(2):148-56.

de Montellano PR, 'Inhibition of Squalene Synthetase by Farnesyl Pyrophosphate Analogues,' J Med Chem, Feb. 1977 (Feb. 1977), 20(2):243-9.

Earl et al., "Ezetimibe", Nature Review, 2003, 2:97-98.

Evans M et al., 'Medical Lipid-Regulating Therapy,' Drugs, 2004 (2004), 64(11):1181-96.

Ex. 2001 to Patent Owner Preliminary Response dated Dec. 8, 2015 in Inter Partes Review Case No. IPR2015-01835 for U.S. Pat. No. 7,932,268 titled "Patent License Agreement between The Trustees of the University of Pennsylvania and Aegerion Pharmaceuticals, Inc.," dated May 19, 2006 (54 pages).

Ex. 2001 to Patent Owner Preliminary Response dated Dec. 8, 2015 in Inter Partes Review Case No. IPR2015-01835 for U.S. Pat. No. 8,618,135 titled "Patent License Agreement between The Trustees of the University of Pennsylvania and Aegerion Pharmaceuticals, Inc.," dated May 19, 2006 (54 pages).

Ex. 2002 to Patent Owner Preliminary Response dated Dec. 8, 2015, IPR2015-01835, "NDA #203858, Sponsor's Background Package for the Endocrinologic and Metabolic Drugs Advisory Committee Meeting, Advisory Committee Briefing Materials (Oct. 17, 2012)."

Ex. 2002 to Patent Owner Preliminary Response dated Dec. 8, 2015, IPR2015-01836, "NDA #203858, Sponsor's Background Package for the Endocrinologic and Metabolic Drugs Advisory Committee Meeting, Advisory Committee Briefing Materials (Oct. 17, 2012)."

Ex. 2003 to Patent Owner Preliminary Response dated Dec. 8, 2015, IPR2015-01835, "ClinicalTrials.gov: Safety, Tolerability, and Efficacy of Microsomal Triglyceride Protein (MTP) Inhibitor, available at https://clinicaltrials.gov/ct2/show/NCT01556906?term=NCT01556906&rank=1."

Ex. 2003 to Patent Owner Preliminary Response dated Dec. 8, 2015, IPR2015-01836, "ClinicalTrials.gov: Safety, Tolerability, and Efficacy of Microsomal Triglyceride Protein (MTP) Inhibitor, available at https://clinicaltrials.gov/ct2/show/NCT01556906?term=NCT01556906&rank=1."

Ex. 2004 to Patent Owner Preliminary Response dated Dec. 8, 2015, IPR2015-01835, "Marina Cuchel et al., *Inhibition of Microsomal Triglyceride Transfer Protein in Familial Hypercholesterolemia*, 356 (2) N. Eng. J. Med. 148-56 (Jan. 11, 2007)."

Ex. 2004 to Patent Owner Preliminary Response dated Dec. 8, 2015, IPR2015-01836, "Marina Cuchel et al., *Inhibition of Microsomal Triglyceride Transfer Protein in Familial Hypercholesterolemia*, 356 (2) N. Eng. J. Med. 148-56 (Jan. 11, 2007)."

Ex. 2005 to Patent Owner Preliminary Response dated Dec. 8, 2015, IPR2015-01835, "U.S. Appl. No. 14/075,483, Amendment and Response to Final Office Action (Nov. 30, 2015)."

Ex. 2005 to Patent Owner Preliminary Response dated Dec. 8, 2015, IPR2015-01836, "U.S. Appl. No. 14/075,483, Amendment and Response to Final Office Action (Nov. 30, 2015)."

Ex. 2006 to Patent Owner Preliminary Response dated Dec. 8, 2015, IPR2015-01835, "FDA News Release, FDA approves new orphan drug for rare cholesterol disorder, available at http://www.fda.gov/NewsEvents/Newsroom/PressAnnouncements/ucm333285.htm (Dec. 26, 2012)."

Ex. 2006 to Patent Owner Preliminary Response dated Dec. 8, 2015, IPR2015-01836, "FDA News Release, FDA approves new orphan drug for rare cholesterol disorder, available at http://www.fda.gov/NewsEvents/Newsroom/PressAnnouncements/ucm333285.htm (Dec. 26, 2012)."

Ex. 2007 to Patent Owner Preliminary Response dated Dec. 8, 2015, IPR2015-01835, "Marina Cuchel et al., *Efficacy and safety of a microsomal triglyceride transfer protein inhibitor in patients with homozygous familial hypercholesterolemia: a single-arm, openlabel, phase 3 study*, 381 The Lancet 40-46 (Jan. 5, 2013)."

Ex. 2007 to Patent Owner Preliminary Response dated Dec. 8, 2015, IPR2015-01836, "Marina Cuchel et al., *Efficacy and safety of a microsomal triglyceride transfer protein inhibitor in patients with homozygous familial hypercholesterolemia: a single-arm, openlabel, phase 3 study*, 381 The Lancet 40-46 (Jan. 5, 2013)."

Ex. 2008 to Patent Owner Preliminary Response dated Dec. 8, 2015, IPR2015-01835, "Joseph Walker et al., *New Hedge Fund Strategy: Dispute the Patent, Short the Stock*, The Wall Street Journal, available at http://www.wsj.com/articles/hedgefundmanagerkylebasschallengesjazzpharmaceuticalspatent1428417408 (Apr. 7, 2015)."

Ex. 2008 to Patent Owner Preliminary Response dated Dec. 8, 2015, IPR2015-01836, "Joseph Walker et al., New Hedge Fund Strategy: Dispute the Patent, Short the Stock, The Wall Street Journal (Apr. 7, 2015), available at http://www.wsj.com/articles/hedgefundmanagerkylebasschallengesjazzpharmaceuticalspatent1428417408."

Ex. 2009 to Patent Owner Preliminary Response dated Dec. 8, 2015, IPR2015-01835, "U.S. Appl. No. 13/046,118: Information Disclosure Statement (IDS) (Sep. 28, 2011)."

Ex. 2010 to Patent Owner Preliminary Response dated Dec. 8, 2015, IPR2015-01835, "Patentee's Observations in reply to the Notice of Opposition by Dr. Evan Stein, European Patent No. 1 725 234 IPR2015-01835 Patent Owner Preliminary Response."

Ex. 2010 to Patent Owner Preliminary Response dated Dec. 8, 2015, IPR2015-01835, "Patentee's Observations in reply to the Notice of Opposition by Dr. Evan Stein, European Patent No. 1 725 234 IPR2015-01836 Patent Owner Preliminary Response."

Ex. 2011 to Patent Owner Preliminary Response dated Dec. 8, 2015, IPR2015-01835, "The Pink Sheet, *MTP inhibitor research discontinued* (Jul. 31, 2000)."

Ex. 2011 to Patent Owner Preliminary Response dated Dec. 8, 2015, IPR2015-01836, "The Pink Sheet, *MTP inhibitor research discontinued* (Jul. 31, 2000)."

Ex. 2012 to Patent Owner Preliminary Response dated Dec. 8, 2015 in Inter Partes Review Case No. IPR2015-01836 for U.S. Pat. No. 7,932,268 titled "U.S. Securities and Exchange Commission Form 10-K [in the name of] Aegerion Pharmaceuticals, Inc.," dated Mar. 2, 2015 (522 pages).

Ex. 2012 to Patent Owner Preliminary Response dated Dec. 8, 2015 in Inter Partes Review Case No. IPR2015-01835 for U.S. Pat. No.

(56) References Cited

OTHER PUBLICATIONS 8,618,135 titled "U.S. Securities and Exchange Commission Form 10-K [in the name of] Aegerion Pharmaceuticals, Inc.," dated Mar. 2, 2015 (522 pages).
Ex. 2013 to Patent Owner Preliminary Response dated Dec. 8, 2015 in Inter Partes Review Case No. IPR2015-01836 for U.S. Pat. No. 7,932,268 6 titled "U.S. Securities and Exchange Commission Form 10-K [in the name of] Aegerion Pharmaceuticals, Inc.," dated Mar. 18, 2013 (133 pages).
Ex. 2013 to Patent Owner Preliminary Response dated Dec. 8, 2015 in Inter Partes Review Case No. IPR2015-01835 for U.S. Pat. No. 8,618,135 titled "U.S. Securities and Exchange Commission Form 10-K [in the name of] Aegerion Pharmaceuticals, Inc.," dated Mar. 18, 2013 (133 pages).
Ex. 2014 to Patent Owner Preliminary Response dated Dec. 8, 2015, IPR2015-01835, "Aegerion Pharmaceuticals, Inc., Third Quarter 2015 Earnings Conference Call, available at http://files.shareholder.com/downloads/AEGR/0x0x860375/8F9C1576-D084-454D-BBCFC656C341E238/AEGR_Q3_15_Slides_Final.pdf (Nov. 9, 2015)."
Ex. 2014 to Patent Owner Preliminary Response dated Dec. 8, 2015, IPR2015-01836, "Aegerion Pharmaceuticals, Inc., Third Quarter 2015 Earnings Conference Call, available at http://files.shareholder.com/downloads/AEGR/0x0x860375/8F9C1576-D084-454D-BBCFC656C341E238/AEGR_Q3_15_Slides_Final.pdf (Nov. 9, 2015)."
Ex. 2015 to Patent Owner Preliminary Response dated Dec. 8, 2015, IPR2015-01835, "Juxtapid label (2012)."
Ex. 2015 to Patent Owner Preliminary Response dated Dec. 8, 2015, IPR2015-01836, "Juxtapid label (2012)."
Ex. 2016 to Patent Owner Preliminary Response dated Dec. 8, 2015, IPR2015-01835, "Center for Drug Evaluation and Research, Application No. 203858Orig1s00, Summary Basis for Regulatory Action (Dec. 21, 2012)."
Ex. 2016 to Patent Owner Preliminary Response dated Dec. 8, 2015, IPR2015-01836, "Center for Drug Evaluation and Research, Application No. 203858Orig1s00, Summary Basis for Regulatory Action (Dec. 21, 2012)."
Excerpt from Clinical Trials.gov, "Implitapide in Patients with Hypertriglyceridemia (HTG) on Maximal, Concurrent Triglyceride-Lowering Therapy," received Mar. 23, 2004.
Expert Panel on Detection, Evaluation, and Treatment of High Blood Cholesterol in Adults. National Cholesterol Education Program: Adult Treatment Panell III Report. Publication No. 01-3095, I-1-IX-11. 2001. Bethesda, MD, National Heart, Lung, and Blook Institute. Ref. Type: Report.
Farrell GC, 'Drugs and Steatohepatitis,' Semin Liver Dis, 2002, 22(2):185-94.
Freidewald, et al. Estimation of the concentration of low density lipoproteincholesterol in plasma without the use of the preparative ultracentrifuge. Clin Chem. 1972; 18:499-502.
Fukushima K et al. "Phase II Clinical Trial: Administration of Novel Antiepileptic Agent, Zonisamide (ZNA), to Epileptic Children," Jap J Pediat, 1987, 40(12):3389-97.
Funatsu et al. "Atorvastatin Increases Hepatic Fatty Acid Beta-Oxidation in Sucrose-Fed Rats: Comparison with an MTP Inhibitor." Eur. J. Pharm. 2002 455:161-167.
Gagné C et al., 'Efficacy and Safety of Ezetimibe Coadministered With Atorvastatin or Simvastatin in Patients With Homozygous Familial Hypercholesterolemia,' Circulation, May 28, 2002 (May 28, 2002), 105(21):2469-75.
Gruetzmann R et al., 'Implitapide (BAY 13-9952) Inhibits Secretion of ApoB-Associated Lipoproteins by Inhibition of the Microsomal Triglyceride Transfer Protein (MTP),' Eur Heart J 2000, Aug. 1, 2000 (Aug. 1, 2000), 21(Abstract Suppl):600 (Abstract# P3271).
Guo, et al. Lipoprotein Lp(a) in homozygous familial hypercholesterolemia: density profile, particle heterogeneity and apolipoprotein(a) phenotype. Atherosclerosis. 1991; 31:6983.
Heider et al., Journal of Lipid Research, 24, 1127 (1983).

Hussain MM et al., 'Multiple Functions of Microsomal Triglyceride Transfer Protein,' Nutr Metab (London), Feb. 21, 2012 (Feb. 21, 2012), 9:14-30.
International Search Report for Application No. PCT/US05/007435 completed Jun. 2, 2005 (Jun. 2, 2005) and dated Jul. 14, 2005 (Jul. 14, 2005), pp. 1-7.
International Search Report for Application No. PCT/US06/040637 completed Mar. 16, 2007 and dated Jun. 12, 2007 (Jun. 12, 2007) pp. 1-8.
International Search Report for Application No. PCT/US06/040639 completed Mar. 22, 2007 (Mar. 22, 2007) and dated Jun. 12, 2007 (Jun. 23, 2007) pp. 1-9.
International Search Report for Application No. PCT/US06/04064 dated May 23, 2007 (9 pages).
International Search Report for Application No. PCT/US06/040640 completed Mar. 13, 2007 (Mar. 13, 2007) and dated May 23, 2007 (May 23, 2007), pp. 1-9.
International Search Report for Application No. PCT/US06/040953 completed Mar. 19, 2007 (Mar. 19, 2007) and mailed Mar. 30, 2007 (Mar. 30, 2007), pp. 1-8.
International Search Report for Application No. PCT/US07/026300 dated Jun. 2, 2008 (4 pages).
Inventor Presentation, Feb. 2004, available electronically Apr. 15, 2004.
Jamil H et al., 'An Inhibitor of the Microsomal Triglyceride Transfer Protein Inhibits ApoB Secretion from HepG2 Cells,' Proc Natl Acad Sci USA, Oct. 15, 1996 (Oct. 15, 1996), 93(21):11991-5.
Japanese Laid-Open Patent Publication No. 2003-321424, English Translation of Abstract and Claims 40 and 52.
Kastelein J, What Future for Combination Therapies?, Int J Clin Pract Suppl 2003, Mar. 2003 (Mar. 2003), 134:45-50.
Kessler, et al. Fluorometric measurement of triglycerides. In: Skeggs LT,Jr, eds. Automation in Analytical Chemistry: Technicom Symposia. New York, NY: Madiad Inc; 1965:341-344.
Kirkpatrick P, 'Fresh From the Pipeline. Market Indicators. Ezetimbe,' Nat Rev Drug Discov, Feb. 2003 (Feb. 2003), 2(2):97-98.
Knopp RH, 'Drug Treatment of Lipid Disorders,' N Engl J Med, Aug. 12, 1999 (Aug. 12, 1999), 341(7):498-511.
Li J et al., 'Discovery of Potent and Orally Active MTP Inhibitors as Potential Anti-Obesity Agents,' Bioorg Med Chem Lett, Mar. 10, 2006 (Mar. 10, 2006), 16(11):3039-42.
Liao W et al., 'Blocking Microsomal Triglyceride Transfer Protein Interferes with ApoB Secretion Without Causing Retention or Stress in the ER,' J Lipid Res, Feb. 16, 2003 (Feb. 16, 2003)(ePub), 44(5):978-85.
Looije NA et al., 'Disodium Ascorbyl Phytostanyl Phosphates (FM-VP4) Reduces Plasma Cholesterol Concentration, Body Weight and Abdominal Fat Gain Within a Dietary-Induced Obese Mouse Model,' J Pharm Pharm Sci, Aug. 24, 2005 (Aug. 24, 2005), 8(3):400-8.
McClard RW and Fujita TS, 'Novel Phosphonylphosphinyl (P-C-P-C-) Analogues of Biochemically Interesting Diphosphates. Synthesis and Properties of P-C-P-C- Analogues of Isopentenyl Diphosphate and Dimethylallyl Diphosphate,' J Am Chem Soc, Sep. 1, 1987 (Sep. 1, 1987), 109(18):5544-5.
Notice of Opposition to European Patent, Aug. 21, 2013.
Orgogozo J-M et al., 'Efficacy and Safety of Memantine in Patients with Mild to Moderate Vascular Dementia. A Randomized, Placebo-Controlled Trial (MMM 300),' Stroke, Jul. 2002 (Jul. 2002), 33(7):1834-9.
Parsons et al., "Memantine is a Clinically Well Tolerated N-Methyl-DAspartate (NMDA) Receptor Antagonist—A Review of Preclinical Data," Neuropharmacology, 38:735-767 (1999).
Patent Owner Preliminary Response filed in Inter Partes Review Case No. IPR2015-01835 for U.S. Pat. No. 8,618,135, dated Dec. 8, 2015, 69 pages.
Patent Owner Preliminary Response filed in Inter Partes Review Case No. IPR2015-01836 for U.S. Pat. No. 7,932,268, dated Dec. 8, 2015, 66 pages.

(56) References Cited

OTHER PUBLICATIONS

Patent Owner's Mandatory Notices Pursuant to 37 C.F.R. §42.8(a)(2) (Paper No. 5) filed in Inter Partes Review Case No. IPR2015-01835 for U.S. Pat. No. 8,618,135, dated Sep. 18, 2015 (5 pages).
Patent Owner's Mandatory Notices Pursuant to 37 C.F.R. §42.8(a)(2) (Paper No. 5) filed in Inter Partes Review Case No. IPR2015-01836 for U.S. Pat. No. 7,932,268, dated Sep. 18, 2015 (5 pages).
Patent Owner's Objections to Evidence Pursuant to 37 C.F.R. §42.64 (Paper No. 9) filed in Inter Partes Review Case No. IPR2015-01835 for U.S. Pat. No. 8,618,135, dated Mar. 21, 2016 (8 pages).
Patent Owner's Objections to Evidence Pursuant to 37 C.F.R. §42.64 (Paper No. 9) filed in Inter Partes Review Case No. IPR2015-01836 for U.S. Pat. No. 7,932,268, dated Mar. 21, 2016 (8 pages).
Patentee's Obsesrvations in reply to the Notice of Opposition filed in European Patent No. 1725234, filed with the European Patent Office on Aug. 27, 2014, 6 pages.
Petition for Inter Partes Review of U.S. Pat. No. 7,932,268, filed Aug. 28, 2015 by the Coalition for Affordable Drugs (ADROCA) LLC ("the ADROCA '268 IPR") (IPR2015-01836).
Petition for Inter Partes Review of U.S. Pat. No. 8,618,135 filed Aug. 28, 2015 by the Coalition for Affordable Drugs (ADROCA) LLC ("the ADROCA '135 IPR") (IPR2015-01835).
Power of Attorney for Coalition for Affordable Drugs VIII LLC (Paper No. 2) filed in Inter Partes Review Case No. IPR2015-01835 for U.S. Pat. No. 8,618,135, dated Aug. 27, 2015 (2 pages).
Power of Attorney for Coalition for Affordable Drugs VIII LLC (Paper No. 2) filed in Inter Partes Review Case No. IPR2015-01836 for U.S. Pat. No. 7,932,268, dated Aug. 27, 2015 (2 pages).
Power of Attorney for Patent Owner The Trustees of the University of Pennsylvania (Paper No. 4) filed in Inter Partes Review Case No. IPR2015-01835 for U.S. Pat. No. 8,618,135, dated Sep. 17, 2015 (3 pages).
Power of Attorney for Patent Owner The Trustees of the University of Pennsylvania (Paper No. 4) filed in Inter Partes Review Case No. IPR2015-01836 for U.S. Pat. No. 7,932,268, dated Sep. 17, 2015 (3 pages).
PTAB, Decision for the Institution of Inter Partes Review, pursuant to 37 C.F.R. § 42.108, of U.S. Pat. No. 7,932,268, (Paper No. 7) entered into the record on Mar. 7, 2016, Case No. IPR2015-01836 (35 pages).
PTAB, Decision for the Institution of Inter Partes Review, pursuant to 37 C.F.R. § 42.108, of U.S. Pat. No. 8,618,135 B2, (Paper No. 7), entered into the record on Mar. 7, 2016, Case No. IPR2015-01835 (35 pages).
PTAB, Notice of Filing Date Accorded to Petition and Time for Filing Patent Owner Preliminary Response, (Paper No. 3), entered into the record on Sep. 8, 2015 in Inter Partes Review Case No. IPR2015-01835, directed to U.S. Pat. No. 8,618,135 B2 (3 pages).
PTAB, Notice of Filing Date Accorded to Petition and Time for Filing Patent Owner Preliminary Response, (Paper No. 3), entered into the record on Sep. 8, 2015 in Inter Partes Review Case No. IPR2015-01836, directed to U.S. Pat. No. 7,932,268 (3 pages).
PTAB, Scheduling Order for Inter Partes Review Case No. IPR2015-01835 and IPR2015-01836 for U.S. Pat. No. 8,618,135 B2 and 7,932,268 B2, respectively, (Paper No. 8), entered into the record on Mar. 7, 2016 (9 pages).
Ritter T et al., 'Heterocyclic Ring Scaffolds as Small-Molecule Cholesterol Absorption Inhibitors,' Org Biomol Chem, Aug. 24, 2005 (Aug. 24, 2005)(ePub), 3(19):3514-23.
Robl JA et al., 'A Novel Series of Highly Potent Benzimidazole-Based Microsomal Triglyceride Transfer Protein Inhibitors,' J Med Chem, Feb. 21, 2001 (Feb. 21, 2001), 44(6):851-6.
Samaha, et al., "Inhibition of Microsomal Triglyceride Transfer Protein Alone or With Ezetimibe in Patients With Moderate Hypercholesterolemia," Nature Clinical Practice, (2008) , pp. 1-9, Nature Publishing Group.
Shiomi M and Ito T, 'MTP Inhibitor Decreases Plasma Cholesterol Levels in LDL Receptor-Deficient WHHL Rabbits by Lowering the VLDL Secretion,' Eur J Pharmacol, Nov. 9, 2001 (Nov. 9, 2001), 431(1):127-31.
So, 'Microsomal Triglyceride Transfer Protein,' Wikipedia Page Microsomal triglyceride transfer protein, Aug. 20, 2013 (Aug. 20, 2013), Wikimedia Foundation, San Francisco, CA, USA (Pub), pp. 1-6, <http://en.wikipedia.org/wiki/Microsomal.triglyceride_transfer_protein>.
Sorbera LA et al., 'Hypolipidemic Treatment of Atherosclerosis MTP Inhibitor ApoB Secretion Inhibitor. Implitapide,' Drugs of the Future, Nov. 2000 (Nov. 2000), 25(11):1138-44.
Sudhop T and von Bergmann K, 'Cholesterol Absorption Inhibitors for the Treatment of Hypercholesterolaemia,' Drug, Sep. 16, 2012 (Sep. 16, 2012), 62(16):2333-47.
Summons to Oral Proceedings in European Pat. No. 1725234, dated Nov. 3, 2014, 13 pages.
Teramoto T et al., "Evaluating Utility[benefit] of Gradual Niceritrol (Perycit®) Titration to Hypercholesterolemia," *Jap Atherosclerosis Soc J: Atherosclerosis*, 1991 (1991), 19(2-3):199-208.
Thomas et al., "Alleviation of MTP Inhibitor-Induced Hepatic Steatosis in Hyperlipidemic fa/fa Rats by Fenofibrate", Dept. of Metabolic Diseases and Dept. of Chemical Research, Boehringer Ingelheim Pharma GmbH & Co. KG.
van Dam, M.J., et al., "Efficacy and Safety of Implitapide (BAY 13 9952), A Microsomal Triglyceride Transfer Protein Inhibitor, in Patients with Primary Hypercholesterolemia," Chapter 2, Dissertation, (2001).
Visioli, "Microsomal triglyceride transfer protein inhibitors," *Current Opinion in Cardiovascular, Pulmonary & Renal Investigational Drugs* (2000), vol. 2, No. 3, pp. 292-293.
Wetterau JR et al., 'An MTP Inhibitor that Normalizes Atherogenic Lipoprotein Levels in WHHL Rabbits,' Science, Oct. 23, 1998 (Oct. 23, 1998), 282(5389):751-4.
Wetterau JR et al., 'Microsomal Triglyceride Transfer Protein,' Biochim Biophys Acta, Apr. 1, 1997 (Apr. 1, 1997), 1345(2):136-50.
Wierzbicki AS, 'New Lipid-Lowering Agents,' Expert Opin Emerging Drugs, Nov. 2003 (Nov. 2003), 8(2):365-76.
Williams SJ and Best JD, 'Novel Microsomal Triglyceride Transfer Protein Inhibitors,' Expert Opin Ther Patents, Apr. 2003 (Apr. 2003), 13(4):479-88.
Zaiss S and Sander E, 'BAY 13-9952 (Implitapide), an Inhibitor of the Microsomal Triglyceride Transfer Protein (MTP), Inhibits Atherosclerosis and Prolongs Lifetime in Apo-E Knockout Mice,' Eur Heart J 2000, Aug. 1, 2000 (Aug. 1, 2000), 21(Abstract Suppl):16 (Abstract #194).

METHODS FOR TREATING DISORDERS OR DISEASES ASSOCIATED WITH HYPERLIPIDEMIA AND HYPERCHOLESTEROLEMIA WHILE MINIMIZING SIDE-EFFECTS

CROSS-REFERENCE TO RELATED APPLICATIONS

This application is a continuation U.S. Ser. No. 15/155,647, filed May 16, 2016, which is a continuation of U.S. Ser. No. 14/959,756, filed Dec. 4, 2015, which is a continuation of U.S. Ser. No. 14/075,483, filed Nov. 8, 2013, which is a continuation of U.S. Ser. No. 13/046,118, filed Mar. 11, 2011, which is a continuation of U.S. Ser. No. 10/591,923, filed Jun. 21, 2007, which is a national phase application under 35 U.S.C. §371 of PCT/US05/007435 filed Mar. 7, 2005 which in turn claims priority benefit of U.S. Ser. No. 60/550,915, filed Mar. 5, 2004, all of which are hereby incorporated by reference in their entireties.

FIELD OF THE INVENTION

The present invention generally relates to therapy for hypercholesterolemia and hyperlipidemia.

BACKGROUND OF THE INVENTION

Hypercholesterolemia is a well-known risk factor for ASCVD, the major cause of mortality in the Western world. Numerous epidemiological studies have clearly demonstrated that pharmacological lowering of total cholesterol (TC) and Low-density Lipoprotein (LDL) Cholesterol (LDL-C) is associated with a significant reduction in clinical cardiovascular events. Hypercholesterolemia is often caused by a polygenic disorder in the majority of cases and modifications in lifestyle and conventional drug treatment are usually successful in reducing cholesterol levels. However, in few cases, as in familial hypercholesterolemia (FH), the cause is a monogenic defect and the available treatment in homozygous patients can be much more challenging and far from optimal because LDL-C levels remain extremely elevated despite aggressive use of combination therapy. Therefore, for this group of high-risk patients, effective medical therapy is urgently needed.

Triglycerides are common types of fats (lipids) that are essential for good health when present in normal amounts. They account for about 95 percent of the body's fatty tissue. Abnormally high triglyceride levels may be an indication of such conditions as cirrhosis of the liver, underactive thyroid (hypothyroidism), poorly controlled diabetes, or pancreatitis (inflammation of the pancreas). Researchers have identified triglycerides as an independent risk factor for heart disease.

Higher-than-normal triglyceride levels are often associated with known risk factors for heart disease, such as low levels of HDL ("good") cholesterol, high levels of LDL ("bad") cholesterol and obesity. Triglycerides may also contribute to thickening of artery walls—a physical change believed to be a predictor of atherosclerosis.

Therefore, high triglyceride levels are at least a warning sign that a patient's heart health may be at risk. In response, physicians may be more likely to stress the importance of losing weight, getting enough exercise, quitting smoking, controlling diabetes and other strategies that patients can use to protect their own cardiovascular health.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias have also been classified into common hypercholesterolemia, familial combined hyperlipidemia, familial hypercholesterolemia, remnant hyperlipidemia, chylomicronemia syndrome and familial hypertriglyceridemia.

A number of treatments are currently available for lowering serum cholesterol and triglycerides. However, each has its own drawbacks and limitations in terms of efficacy, side-effects and qualifying patient population.

Bile-acid-binding resins are a class of drugs that interrupt the recycling of bile acids from the intestine to the liver; e.g., cholestyramine (Questran Light®, Bristol-Myers Squibb), and colestipol hydrochloride (Colestid®, The Upjohn Company). When taken orally, these positively-charged resins bind to the negatively charged bile acids in the intestine. Because the resins cannot be absorbed from the intestine, they are excreted carrying the bile acids with them. The use of such resins, however, at best only lowers serum cholesterol levels by about 20%, and is associated with gastrointestinal side-effects, including constipation and certain vitamin deficiencies. Moreover, since the resins bind other drugs, other oral medications must be taken at least one hour before or four to six hours subsequent to ingestion of the resin; thus, complicating heart patient's drug regimens.

The statins are cholesterol-lowering agents that block cholesterol synthesis by inhibiting HMGCoA reductase—the key enzyme involved in the cholesterol biosynthetic pathway. The statins, e.g., lovastatin (Mevacor®, Merck & Co., Inc.), simvastatin (Zocor®, Merck & Co., Inc.), atorvastatin (Lipitor®, Pfizer), rosuva (Crestor®, Astra Zeneca) and pravastatin (Pravachol®, Bristol-Myers Squibb Co.), and combinations thereof, are sometimes used in combination with bile-acid-binding resins. Statins significantly reduce serum cholesterol and LDL-serum levels, and slow progression of coronary atherosclerosis. However, serum HDL cholesterol levels are only moderately increased. The mechanism of the LDL lowering effect may involve both reduction of VLDL concentration and induction of cellular expression of LDL-receptor, leading to reduced production and/or increased catabolism of LDLs. Side effects, including liver and kidney dysfunction are associated with the use of these drugs (Physicians Desk Reference, Medical Economics Co., Inc., Montvale, N.J., 2004; hereinafter "PDR"). The FDA has approved atorvastatin to treat rare but urgent cases of familial hypercholesterolemia.

Ezetimibe is a cholesterol absorption inhibitor which reduces the amount of cholesterol absorbed by the body. Ezetimibe is used to reduce the amount of total cholesterol, LDL cholesterol (by about 18%), and apolipoprotein B. Ezetimibe is often used with a low cholesterol diet and, in some cases, other cholesterol lowering medications.

Niacin, or nicotinic acid, is a water soluble vitamin B-complex used as a dietary supplement and antihyperlipidemic agent. Niacin diminishes production of VLDL and is effective at lowering LDL. In some cases, it is used in combination with bile-acid binding resins. NIASPAN® has been approved to prevent recurrent heart attacks in patients with high cholesterol. Niacin can increase HDL when used at adequate doses, however, its usefulness is limited by serious side effects when used at such high doses.

Fibric acid derivatives ("fibrates") are a class of lipid-lowering drugs used to treat various forms of hyperlipidemia (i.e., elevated serum triglycerides) which may also be associated with hypercholesterolemia. Fibrates appear to reduce the VLDL fraction and modestly increase HDL. However, the effects of these drugs on serum cholesterol is variable. Fibrates are mainly used to lower high triglyceride levels. Although fibrates typically do not appear as effective as statins in lowering total cholesterol and LDL cholesterol levels, they are sometimes used in combination with statins or other medications to lower very high cholesterol levels. For example, fibrates are also sometimes added to statins to raise HDL cholesterol levels. In the United States, fibrates have been approved for use as antilipidemic drugs, but have not received approval as hypercholesterolemia agents. For example, clofibrate (Atromid-S®, Wyeth-Ayerst Laboratories) is an antilipidemic agent which acts to lower serum triglycerides by reducing the VLDL fraction. Although serum cholesterol may be reduced in certain patient subpopulations, the biochemical response to the drug is variable, and is not always possible to predict which patients will obtain favorable results. Atromid-S® has not been shown to be effective for prevention of coronary heart disease. The chemically and pharmacologically related drug, gemfibrozil (Lopid®, Parke-Davis) is a lipid regulating agent which moderately decreases serum triglycerides and VLDL cholesterol, and moderately increases HDL cholesterol—the $HDL_2$ and $HDL_3$ subfractions as well as both ApoA-I and A-II (i.e., the AI/AII-HDL fraction). However, the lipid response is heterogeneous, especially among different patient populations. Moreover, while prevention of coronary heart disease was observed in male patients between 40-55 without history or symptoms of existing coronary heart disease, it is not clear to what extent these findings can be extrapolated to other patient populations (e.g., women, older and younger males). Indeed, no efficacy was observed in patients with established coronary heart disease. Fenofibrate (Tricor, Secalip) is also used to reduce levels of cholesterol and triglycerides. Serious side-effects have been associated with the use of several fibrates including toxicity such as malignancy, (especially gastrointestinal cancer), gallbladder disease and an increased incidence in non-coronary mortality. Fibrates are often not indicated for the treatment of patients with high LDL or low HDL as their only lipid abnormality (Physician's Desk Reference, 2004, Medical Economics Co., Inc. Montvale, N.J.).

Oral estrogen replacement therapy may be considered for moderate hypercholesterolemia in post-menopausal women. However, increases in HDL may be accompanied with an increase in triglycerides. Estrogen treatment is, of course, limited to a specific patient population (postmenopausal women) and is associated with serious side effects including induction of malignant neoplasms, gall bladder disease, thromboembolic disease, hepatic adenoma, elevated blood pressure, glucose intolerance, and hypercalcemia.

Homozygous familial hypercholesterolemia (hoFH) is a serious life-threatening genetic disease caused by homozygosity or compound heterozygosity for mutations in the low density lipoprotein (LDL) receptor. Total plasma cholesterol levels are generally over 500 mg/dl and markedly premature atherosclerotic vascular disease is the major consequence. Untreated, most patients develop atherosclerosis before age 20 and generally do not survive past age 30. The primary goal of therapy consists of controlling the hypercholesterolemia to delay the development of atherosclerotic cardiovascular disease (ASCVD). However, patients diagnosed with hoFH are largely unresponsive to conventional drug therapy and have limited treatment options. A mean LDL-C reduction of only about 5.5% has been recently reported in patients with genotype-confirmed hoFH treated with the maximal dose of statins (atorvastatin or simvastatin 80 mg/day). The addition of ezetimibe 10 mg/day to this regimen resulted in a total reduction of LDL-C levels of 27%, which is still far from optimal. Several non-pharmacological options have also been tested. Surgical interventions, such as portacaval shunt and ileal bypass have resulted only in partial and transient LDL-C lowering. Orthotopic liver transplantation has been demonstrated to substantially reduce LDL-C levels in hoFH patients, but obvious disadvantages and risks are associated with this approach. Although hoFH could be an excellent model for gene therapy, this modality of treatment is not foreseeable in the near future due to the limitations on the availability of safe vectors that provide long-term expression of LDL receptor gene. Thus, the current standard of care in hoFH is LDL apheresis, a physical method of filtering the plasma of LDL-C which as monotherapy can transiently reduce LDL-C by about 50%. Apheresis uses affinity columns to selectively remove apoB-containing lipoproteins. However, because of rapid re-accumulation of LDL-C in plasma, apheresis has to be repeated frequently (every 1-2 weeks) and requires 2 separate sites for IV access. Although anecdotally this procedure may delay the onset of atherosclerosis, it is laborious, expensive, and not readily available. Furthermore, although it is a procedure that is generally well tolerated, the fact that it needs frequent repetition and IV access can be challenging for many of these young patients. Therefore, there is a tremendous unmet medical need for new medical therapies for hoFH.

Patients with heterozygous FH can usually be successfully treated with combination drug therapy to lower the LDL-C to acceptable levels. In contrast, hoFH is unresponsive to conventional drug therapy and thus there are limited treatment options. Specifically, treatment with statins, which reduce LDL-C by inhibiting cholesterol synthesis and upregulating the hepatic LDL receptor, have negligible effect in patients whose LDL receptors are non-existent or defective.

In July 2004, the NCEP published a paper entitled "Implications of Recent Clinical Trials for the National Cholesterol Education Program Adult Treatment Panel III Guidelines", updating certain elements of the "Adult Treatment Panel III (ATP III)" cholesterol guidelines released in 2001. For high-risk patients, individuals who have coronary heart disease (CHD) or disease of the blood vessels to the brain or extremities, or diabetes, or multiple (2 or more) risk factors that give them a greater than 20 percent chance of having a heart attack within 10 years, the ATP III update recommends that the overall goal for high-risk patients is still an LDL less than 100 mg/dL with a therapeutic option to set the goal at an LDL less than 70 mg/dL for very high-risk patients, those who have had a recent heart attack, or those who have cardiovascular disease combined with either diabetes, or severe or poorly controlled risk factors (such as continued smoking), or metabolic syndrome (a cluster of risk factors associated with obesity that includes high triglycerides and low HDL cholesterol). The ATP III update also recommends consideration of drug treatment in addition to lifestyle therapy for LDL levels 100 mg/dL or higher in high-risk patients, and characterizes drug treatment as optional for LDL less than 100 mg/dL. For moderately high-risk patients, individuals who have multiple (2 or more) CHD risk factors together with a 10-20 percent risk for a heart attack within 10 years, the ATP III update recommends the overall goal for moderately high-risk patients to be an LDL less than 130 mg/dL. There is a therapeutic option to set the treatment goal at an LDL less than 100 mg/dL, and to use drug treatment if LDL is 100-129 mg/dL. For high-risk and moderately high-risk patients, the ATP III update advises that the intensity of LDL-lowering drug treatment in high-risk and moderately high-risk patients be sufficient to achieve at least a 30 percent reduction in LDL levels.

Patients suffering from severe hypercholesterolemia may also be unable to reach the new goals for LDL and HDL described above. For example, a large number of patients may be unable to attain LDL levels less than 70 using maximally tolerated current methodologies.

Abetalipoproteinemia is a rare genetic disease characterized by extremely low cholesterol and TG levels, absent apolipoprotein (apo) B-containing lipoproteins in plasma, fat malabsorption, severe vitamin E deficiency, and progressive spinocerebellar and retinal degeneration. It has been determined that mutations in the MTP were the genetic cause of abetalipoproteinemia. MTP is responsible for transferring lipids, particularly TG, onto the assembling chylomicron and VLDL particles in the intestine and the liver, respectively. Although the mechanisms by which lipoproteins are formed are not completely understood, it is currently believed that the assembly of apoB containing lipoproteins requires two steps. The first step occurs within the endoplasmic reticulum that involves the synthesis of particles that contain only a small fraction of the lipid core found in the secreted lipoprotein. A larger core of lipid is added to the nascent particle in a second step. MTP is thought to be essential for the transfer of lipid to the apoB during the first step of the process. In the absence of functional MTP, chylomicrons and VLDL are not effectively assembled or secreted in the circulation and apoB is likely targeted for degradation. VLDL serves as the metabolic precursor to LDL and the inability to secrete VLDL from the liver results in the absence of LDL in the blood. The concept that MTP may regulate apoB lipoprotein assembly is supported by observations in mice models. In heterozygous knockout mice MTP mRNA, protein and activity have been reported approximately half of normal and the apoB plasma concentration was reduced about 30%. Dramatic reduction of apoB-100 concentration in plasma was also seen in liver-specific MTP knockout mice. The finding that MTP is the genetic cause of abetaliproteinemia and that is involved in apoB-containing particles assembly and secretion led to the concept that pharmacologic inhibition of MTP might be a successful strategy for reducing atherogenic lipoproteins levels in humans.

Because of the tremendous impact on the treatment of atherosclerosis and cardiovascular disease that can be derived from the pharmacologic inhibition of hepatic secretion of apoB containing lipoproteins, several MTP inhibitors have been developed. Both in vitro and in vivo animal studies with these compounds support the concept that inhibition of MTP results in inhibition of apoB containing lipoproteins secretion and consequent reduction of plasma cholesterol levels. Interestingly, the animal studies cited above had been conducted in Watanabe-heritable hyperlipidemic (WHHL) rabbits and LDLR-/- mice, two models for hoFH.

Bristol-Myers Squibb (BMS) developed a series of compounds, including BMS-201038, as potent inhibitors of MTP-mediated neutral lipid transfer activity. These compounds are described, for example, in U.S. Pat. Nos. 5,789,197, 5,883,109, 6,066,653, and 6,492,365, each of which is incorporated herein by reference in its entirety. MTP inhibitors are described throughout U.S. Pat. No. 6,066,653, in particular in columns 3-28. In in vitro studies, BMS-201038 appears to inhibit lipid transfer by directly binding to MTP. In cell culture studies, the $IC_{50}$ for inhibition of apoB secretion by BMS-201038 was much lower than that for apoAI secretion (0.8 nM vs 6.5 µM), indicating that the compound is a highly selective inhibitor of apoB secretion. The efficacy to inhibit accumulation of triglyceride-rich particles in plasma of rats after injection of Triton is similar in both fed and fasted states, suggesting that both intestinal and hepatic lipoprotein secretions are inhibited by this compound. Six-month toxicity studies were conducted by BMS in rats and dogs and their results are detailed in IND#50,820. Doses tested were 0, 0.02, 0.2, 2.0, and 20 mg/kg in rats and 0, 0.01, 0.1, 1.0, and 10 mg/kg in dogs. Dose-related lipid accumulation in the liver and small intestine correlated with decrease in serum TG and cholesterol levels. These changes are a consequence of the pharmacologic effects of BMS-201038. In rats, but not in dogs, doses of 0.2 mg/kg and higher were associated with subacute inflammation and single-cell necrosis of hepatocytes and histiocytosis (phospholipidosis) in the lungs. The hepatic accumulation of lipids was reversed in rats at the end of a 1-month washout period. Studies in animals indicated that BMS-201038 effectively reduced plasma cholesterol levels in a dose dependent manner. BMS-201038 was found to be effective in reducing cholesterol levels in rabbits that lack a functional LDL receptor: The $ED_{50}$ value for lowering cholesterol was 1.9 mg/kg and a dose of 10 mg/kg essentially normalized cholesterol levels with no alteration in plasma AST or ALT. This study, conducted in the best accepted animal model for the homozygous FH, indicated that MTP inhibition by BMS-201038 might be effective in substantially reducing cholesterol levels in patients with hoFH.

Clinical development of BMS-201038 as a drug for large scale use in the treatment of hypercholesterolemia has been discontinued, because of significant and serious hepatotoxicities. For example, gastrointestinal side effects, elevation of serum transaminases and hepatic fat accumulation were observed, primarily at 25 mg/day or higher doses. Thus, there is a need to develop methods for treating hyperlipidemia and/or hypercholesterolemia that are efficacious in lowering serum cholesterol and LDL, increasing HDL serum levels, preventing coronary heart disease, and/or treating diseases associated with hyperlipidemia and/or hypercholesterolemia, without the side-effects associated with known treatments.

SUMMARY OF THE INVENTION

The present invention relates to methods of treating disorders associated with hypercholesterolemia and/or hyperlipidemia.

In some embodiments the invention relates to methods of treating a subject suffering from a disorder associated with hyperlipidemia and/or hypercholesterolemia. The methods comprise administering to the subject an amount of an MTP inhibitor effective to ameliorate the disorder, wherein said administration comprises at least three step-wise, increasing dosages of the MTP inhibitor. In some embodiments the MTP inhibitor has the structure:

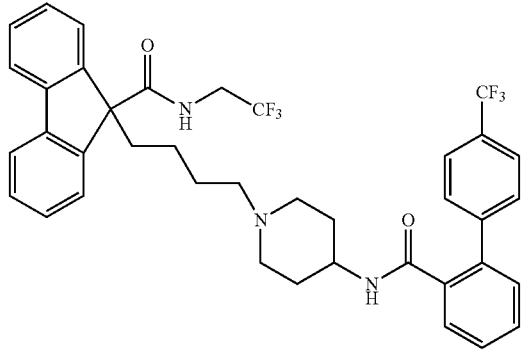 [SMILES: O=C(NC1CCN(CCCCC2(C(=O)NCC(F)(F)F)c3ccccc3-c3ccccc32)CC1)c1ccccc1-c1ccc(C(F)(F)F)cc1]

or a pharmaceutically acceptable salt thereof or the piperidine N-oxide thereof.

The present invention further provides methods for inhibiting MTP in a subject in need thereof. The methods comprise administering to the subject an amount of an MTP inhibitor effective to inhibit MTP, wherein said administration comprises at least three step-wise, increasing dosages of the MTP inhibitor.

The present invention provides kits for treating a disorder associated with hyperlipidemia and/or hypercholesterolemia in a subject, comprising at least three sets of pharmaceutical dosage units; and instructions for use.

DETAILED DESCRIPTION OF THE INVENTION

The present invention is based on the surprising discovery that one may treat an individual who has hyperlipidemia and/or hyperlcholesterolemia with an MTP inhibitor in a manner that results in the individual not experiencing side-effects normally associated with the inhibitor, or experiencing side-effects to a lesser degree. Accordingly, the present invention provides methods of treating a subject suffering from a disorder associated with hyperlipidemia while reducing side-effects, the method comprising the step of administering to the subject an effective amount of the MTP inhibitor to ameliorate hyperlipidemia and/or hypercholesterolemia in the subject according to a treatment regimen that reduces and/or eliminates side-effects associated with the use of the inhibitors.

By "treatment" is meant at least an amelioration of the symptoms associated with the pathological condition afflicting the host as well as an amelioration of the side-effects associated with the MTP inhibitor seen in patients treated in accordance with traditional treatment regimens making use of MTP inhibitors. "Amelioration" is used in a broad sense to refer to at least a reduction in the magnitude of a parameter, e.g. symptom, associated with the pathological condition being treated, such as elevated plasma VLDL or triglyceride levels, or with a side effect of treatment using the inhibitor, such as GI side-effects or hepatobiliary side-effects. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition, e.g. plasma VLDL and/or triglyceride levels are returned to normal.

The present invention also provides methods of treating diseases/disorders associated with hypercholesterolemia and/or hyperlipidemia comprising administering to a subject an MTP inhibitor and a further lipid modifying compound. The methods reduce and/or eliminate side-effects associated with the use of MTP inhibitors.

As used herein, the phrase "disorders associated with hyperlipidemia and/or hypercholesterolemia" refers to diseases and disorders related to or caused by elevated lipid or cholesterol levels. Such diseases and disorders include, without limitation, hypercholesterolemia, severe hypercholesterolemia, familial combined hyperlipidemia, familial hypercholesterolemia, remnant hyperlipidemia, chylomicronemia syndrome and familial hypertriglyceridemia. In some embodiments, the disease is severe hypercholesterolemia. In some embodiments, the disease is homozygous/heterozygous familial hypercholesterolemia. In some embodiments the disease is hypertriglyceridemia.

Microsomal triglyceride transfer protein (MTP) is known to catalyze the transport of triglyceride and cholesteryl ester by preference to phospholipids such as phosphatidylcholine. It was demonstrated by D. Sharp et al., Nature (1993) 365:65 that the defect causing abetalipoproteinemia is in the MTP gene. This indicates that MTP is required for the synthesis of Apo B-containing lipoproteins such as VLDL, the precursor to LDL. It therefore follows that an MTP inhibitor would inhibit the synthesis of VLDL and LDL, thereby lowering levels of VLDL, LDL, cholesterol and triglyceride in humans.

MTP inhibitors belong to the class of polyarylcarboxamides. MTP inhibitors, methods of use and preparation thereof are known to the art skilled and are described, inter alia, in WO 96/26205; U.S. Pat. No. 5,760,246; WO 96/40640; WO-98/27979. Canadian Patent Application Ser. No. 2,091,102, U.S. application Ser. No. 117,362, WO 92/26205 published Aug. 29, 1996, U.S. application Ser. No. 472,067, filed Jun. 6, 1995, U.S. application Ser. No. 548,811, filed Jan. 11, 1996, U.S. provisional application Ser. No. 60/017,224, filed May 9, 1996, U.S. provisional application Ser. No. 60/017,253, filed May 10, 1996, U.S. provisional application Ser. No. 60/017,254, filed May 10, 1996, U.S. provisional application Ser. No. 60/028,216, filed Oct. 1, 1996, U.S. Pat. No. 5,595,872, U.S. Pat. No. 5,789,197, U.S. Pat. No. 5,883,109, and U.S. Pat. No. 6,066,653. All of the above, including structures, are incorporated herein by reference.

Pharmacologic inhibition of MTP with Bristol-Myers Squibb's BMS-201038, a potent inhibitor of MTP, has been shown to reduce low density lipoprotein cholesterol (LDL-C) by up to 65% in healthy volunteers with hypercholesterolemia. Despite these impressive LDL-C reductions, steatorrhea, elevation of serum transaminases and hepatic fat accumulation were observed, primarily at 25 mg/day or higher doses. Thus, Bristol-Myers Squibb decided that these side effects made it unlikely that BMS-201038 could be developed as a drug for large scale use in the treatment of hypercholesterolemia. Combinations using MTP inhibitors and other cholesterol or triglyceride drugs have been previously disclosed (U.S. Pat. Nos. 6,066,653 and 5,883,109) but suffer the same drawbacks as described above for MTP inhibitors used alone.

In some embodiments the MTP inhibitors are piperidine, pyrrolidine or azetidine compounds. In some embodiments, the MTP inhibitor has a structure as set forth in U.S. Pat. No.

6,066,653. In some embodiments the MTP inhibitor is 9-[4-[4-[[2-(2,2,2-trifluoromethyl)-benzoyl]amino]-1-piperidinyl]butyl]-N-(2,2,2-trifluoroethyl)-9H-fluorene-9-carboxamide. In some embodiments, the MTP inhibitor is BMS-201038. As used herein, the phrase "BMS-201038" refers to a compound known as N-(2,2,2-Trifluoroethyl)-9-[4-[4-[[[4'-(trifluoromethyl) [1,1'biphenyl]-2-Yl]carbonyl]amino]-1-piperidinyl]butyl]9H-fluorene-9-carboxamide, methanesulfonate, having the formula:

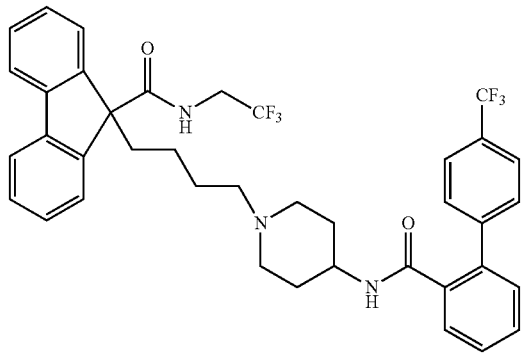 [SMILES: O=C(NC1CCN(CCCCC2(C(=O)NCC(F)(F)F)c3ccccc3-c3ccccc32)CC1)c1ccccc1-c1ccc(C(F)(F)F)cc1]

or a pharmaceutically acceptable salt thereof or the piperidine N-oxide thereof.

In some embodiments, MTP activity is inhibited by 10%, 20%, 25%, 30%, 40%, 50%, 60%, 70%, 75%, 80, 90%, 95%, or 100% compared to a MTP activity in an untreated or control subject. Methods for testing for inhibition of MTP activity are known to those of skill in the art and are set forth, for example, in U.S. Pat. No. 5,789,197.

As used herein, the phrase "untreated or control subject" refers to a subject who has not been administered an MTP inhibitor in at least three step-wise, increasing dosages.

In some embodiments, the methods further comprise the administration of other lipid modifying compounds. As used herein, the phrase "lipid modifying compounds" and the like, refers to medicaments for treating disorders associated with hypercholesterolemia and/or hyperlipidemia using standard dosing, e.g. a treatment not including at least three step-wise, increasing dosages of an MTP inhibitor. Lipid modifying compounds which may be used in the method of the invention include, without limitation, HMG CoA reductase inhibitors, cholesterol absorption inhibitors, ezetimibe, squalene synthetase inhibitors, fibrates, bile acid sequestrants, statins, probucol and derivatives, niacin, niacin derivatives, PPAR alpha agonists, fibrates, PPAR gamma agonists, thiazolidinediones, and cholesterol ester transfer protein (CETP) inhibitors.

HMG CoA reductase inhibitors suitable for use herein include, but are not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171, with pravastatin, lovastatin or simvastatin being preferred. Other HMG CoA reductase inhibitors which may be employed herein include, but are not limited to, fluvastatin, rosuva, cerivastatin, atorvastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-di-substituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors. In addition, phosphinic acid compounds useful in inhibiting HMG CoA reductase suitable for use herein are disclosed in GB 2205837.

Squalene synthetase inhibitors suitable for use herein include, but are not limited to, α-phosphonosulfonates disclosed in U.S. application Ser. No. 08/266,888, filed Jul. 5, 1994 (HX59b), those disclosed by Biller et al, J. Med. Chem. 1988, Vol. 31, No. 10, pp 1869-1871, including isoprenoid (phosphinylmethyl)phosphonates including the triacids thereof, triesters thereof and tripotassium and trisodium salts thereof as well as other squalene synthetase inhibitors disclosed in U.S. Pat. Nos. 4,871,721 and 4,924,024 and in Biller et al, J. Med. Chem., 1988, Vol. 31, No. 10, pp 1869 to 1871.

In addition, other squalene synthetase inhibitors suitable for use herein include the terpenoid pyrophosphates disclosed by P. Ortiz de Montellano et al, J. Med. Chem.; 1977, 20, 243-249, the farnesyl diphosphate analog A and presqualene pyrophosphate (PSQ-PP) analogs as disclosed by Corey and Volante, (J. Am. Chem. Soc. 1976, 98, 1291-1293), phosphinylphosphonates reported by McClard, R. W. et al, (J.A.C.S., 1987, 109, 5544) and cyclopropanes reported by Capson, T. L., (PhD dissertation, June, 1987, Dept. Med. Chem. U. of Utah, Abstract, Table of Contents, pp. 16, 17, 40-43, 48-51, Summary). In some embodiments the inhibitor is pravastatin, lovastatin or simvastatin.

Peroxisome proliferator activated receptor-alpha (PPAR-alpha) and PPAR-gamma agonists, fibrates, thiazolidinediones and CETP inhibitors are well known to those skilled in the art.

The present invention provides methods for treating diseases or disorders associated with hyperlipidemia and/or hypercholesterolemia while minimizing side-effects ordinarily associated with the use of such inhibitors. In some embodiments, the inhibitor is an MTP inhibitor having the structure:

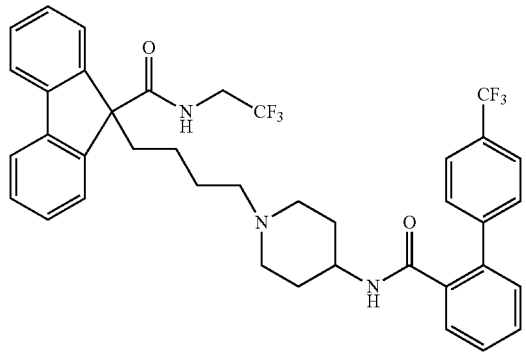 [SMILES: O=C(NC1CCN(CCCCC2(C(=O)NCC(F)(F)F)c3ccccc3-c3ccccc32)CC1)c1ccccc1-c1ccc(C(F)(F)F)cc1]

In some embodiments, one or more of total cholesterol levels, plasma LDL-cholesterol levels, triglyceride levels, fasting triglycerides (TG) levels, VLDL levels, lipoprotein (a) (Lp(a)) levels, or Apolipoproteins A-I, A-II, B, and E levels in the subject are reduced by at least 15%, by at least 25%, at least 30%, at least 40%, at least 50%, at least 60%, at least 70%, at least 75%, or at least 80% compared to control blood levels.

In some embodiments, triglyceride levels achieved are less than 500 mg/dl. In some embodiments, triglyceride levels achieved are less than 300 mg/dl. In some embodiments, triglyceride levels achieved are less than 200 mg/dl. In some embodiments, triglyceride levels achieved are less than 150 mg/dl.

In some embodiments, the ApoB/ApoA1 ratio achieved by treatment according to the present invention is from 0.25 to 1.25. In some embodiments the ApoB/ApoA1 ratio achieved is from 0.1 to 2.0. In some embodiments the apoB level achieved is from 48-130. In some embodiments the apoB level achieved is from 20-180.

As used herein, the phrase "control blood levels" refers to a level of a particular blood component in the absence of treatment according to the present invention. In some embodiments, the "control blood level" is the level of a particular blood component in the subject prior to treatment of the subject according to the present invention. In some embodiments, the "control blood level" is the level of a particular blood component if a subject either receiving a placebo or receiving a different treatment; e.g. a treatment not including at least three step-wise, increasing dosages of an MTP inhibitor. Reduction of levels of blood components, including, for example, cholesterol, triglycerides, and apolipoprotein B, can be determined by comparing pre-treatment levels to levels during or after treatment according to the present invention. Methods of measuring levels of particular components of blood are well-known to those of skill in the art. For example, total plasma cholesterol and triglyceride concentrations may be determined by a modification of the Liebermann-Burchard reaction (Abell L L, Levy B B, Brodie B B, Kendall F E. A simplified method for the estimation of total cholesterol in serum and demonstration of its specificity. *J Biol Chem.* 1952; 195:357-362) and by the method of Kessler and Lederer after zeolite extraction, (Kessler G, Lederer H. Fluorometric measurement of triglycerides. In: Skeggs L T, Jr, eds. *Automation in Analytical Chemistry: Technicom Symposia.* New York, N.Y.: Madiad Inc; 1965:341-344), respectively. Plasma HDL cholesterol may be estimated by the method of Allain et al (Allain C C, Poon L S, Chan G S G, Richmond W, Fu P C. Enzymatic determination of total serum cholesterol. *Clin Chem.* 1974; 20:470-475) using an enzymatic kit (Biotrol). LDL cholesterol may be calculated using the Freidewald formula. (Freidewald W T, Levy R I, Fredrickson D S. Estimation of the concentration of low density lipoprotein-cholesterol in plasma without the use of the preparative ultracentrifuge. *Clin Chem.* 1972; 18:499-502). Plasma apoB, apoA1, and lipoprotein(a) levels may be measured by immunological assays as described earlier (Guo H, Chapman M J, Bruckert E, Farriaux J P, De Gennes J L. Lipoprotein Lp(a) in homozygous familial hypercholesterolemia: density profile, particle heterogeneity and apolipoprotein(a) phenotype. *Atherosclerosis.* 1991; 31:69-83) and based on laser immunonephelometry (Immuno AG).

In some embodiments, the subject is a mammal, preferably a human. In some embodiments, the subject has proven refractory to previous treatment regimens.

The MTP inhibitors of the present invention may be used alone or optionally in combination with other lipid modifying compounds and may be administered systemically, such as orally or parenterally or transdermally, to subjects in need of treatment. The dosages and formulations for the other lipid modifying compounds to be employed, where applicable, will be as set out in the latest edition of the Physicians' Desk Reference.

As used herein, the term "susceptible" refers to patients who suffer one or more side-effects when MTP inhibitors are administered to them using traditional treatment regimens in an attempt to ameliorate hypercholesterolemia and/or hyperlipidemia.

As used herein, the phrase "traditional treatment regimens" and the like, refers to methods of treating hypercholesterolemia and/or hyperlipidemia using standard dosing, e.g. a treatment not including at least three step-wise, increasing dosages of an MTP inhibitor.

Although not wishing to be bound by theory, it is thought that the administration of MTP inhibitors in accordance with the methods of the present invention, in combination with one or more other lipid modifying compounds may further reduce undesired levels of cholesterol or lipids and/or reduce undesired side-effects of the MTP inhibitor or undesired side-effects of the MTP inhibitor and the other lipid modifying compounds.

In some embodiments, the MTP inhibitor is administered at escalating doses. In some embodiments, the escalating doses comprise at least a first dose level and a second dose level. In some embodiments, the escalating doses comprise at least a first dose level, a second dose level, and a third dose level. In some embodiments, the escalating doses further comprise a fourth dose level. In some embodiments, the escalating doses comprise a first dose level, a second dose level, a third dose level, a fourth dose level and a fifth dose level. In some embodiments, six, seven, eight, nine and ten dose levels are contemplated.

In some embodiments, each dose level is no more than 50% of the immediately following dose level. In some embodiments, each dose level is no more than 33% of the immediately following dose level. In some embodiments, each dose level is no more than 20% of the immediately following dose level. In some embodiments, dose levels are separated by ½ log units. In some embodiments, dose levels are separated by 1 log unit.

In some embodiments, the first dose level is from about 0.02 to about 0.059 mg/kg/day. In some embodiments, second dose level is from about 0.06 to about 0.19 mg/kg/day. In some embodiments, the third dose level is from about 0.2 to about 0.59 mg/kg/day. In some embodiments, the fourth dose level is from about 0.6 to about 2.0 mg/kg/day.

In some embodiments the MTP inhibitor is administered to the subject at:

(a) 0.03 mg/kg/day for a first interval;
(b) 0.1 mg/kg/day for a second interval;
(c) 0.3 mg/kg/day for a third interval; and
(d) 1.0 mg/kg/day for a fourth interval.

In some embodiments the first, second, third, and fourth dose levels are administered to the subject for from about 2 days to about 6 months in duration. In some embodiments the first, second, third, and fourth dose levels are administered to the subject for from about 7 days to about 35 days in duration. In some embodiments the first, second, third, and fourth dose levels are administered to the subject for from about 2 weeks to about 4 weeks in duration. In some embodiments the first, second, third, and fourth dose levels are administered to the subject for about 4 weeks. In some embodiments the first, second, third dose levels are administered to the subject for from about 2 days to about 40 days and the fourth dose level is administered to the subject for from about 2 days to about 6 months.

In some embodiments, the first dose level is from about 2 to about 30 mg/day. In some embodiments, the second dose level is from about 20 to about 50 mg/day. In some embodiments, the third dose level is from about 30 to about 60 mg/day. In some embodiments, the fourth dose level is from about 40 to about 75 mg/day. In some embodiments, the fifth dose level is from about 50 to about 75 mg/day.

In some embodiments, the first dose level is from about 2 to about 13 mg/day. In some embodiments, the second dose level is from about 5 to about 30 mg/day. In some embodiments, the third dose level is from about 10 to about 50 mg/day. In some embodiments, the fourth dose level is from about 20 to about 60 mg/day. In some embodiments, the fifth dose level is from about 30 to about 75 mg/day.

In some embodiments the first dose level is 6.25 mg/day, the second dose level is 12.5 mg/day, and the third dose level is 50 mg/day.

In some embodiments the first dose level is about 12.5 mg/day. In some embodiments, the second dose level is about 25 mg/day. In some embodiments, the third dose level is from about 37.5 mg/day. In some embodiments, the fourth dose level is about 50 mg/day.

In some embodiments the first dose level is about 25 mg/day. In some embodiments, the second dose level is about 37.5 mg/day. In some embodiments, the third dose level is from about 50 mg/day. In some embodiments, the fourth dose level is about 75 mg/day.

In some embodiments the methods comprise the administration of five or more escalating doses to the subject. In some embodiments the first dose level is 6.25 mg/day, the second dose level is 12.5 mg/day, the third dose level is 25 mg/day, the fourth dose level is 37.5 mg/day, and the fifth dose level is 50 mg/day.

In some embodiments each dose level is administered to the subject for from 2 days to 26 weeks. In some embodiments each dose level is administered to the subject for from about 1 week to about 26 weeks. In some embodiments each dose level is administered to the subject for from about 1 week to about 12 weeks. In some embodiments, each dose level is administered to the subject for 1 week to 5 weeks. In some embodiments each dose level is administered to the subject from 1 to 4 weeks. In some embodiments each dose level is administered to the subject from 1 to 2 weeks. In some embodiments each dose level is administered to the subject from 1 to 2 weeks.

In some embodiments the first dose level is administered to the subject for 1 week, the second dose level is administered to the subject for 1 week, and the third dose level is administered to the subject for 1 week.

In some embodiments the first dose level is administered to the subject for 2 weeks, the second dose level is administered to the subject for 2 weeks, and the third dose level is administered to the subject for 2 weeks.

In some embodiments, the other lipid modifying compounds are administered according to traditional treatment regimens. In some embodiments, the lipid modifying compounds are administered at escalating doses. In some embodiments, the lipid modifying compounds are administered to the subject in least three step-wise, increasing dosages.

As used herein, the phrase "minimizing side effects" refers to an amelioration or elimination of one or more undesired side effects of the MTP inhibitors of the present invention.

As used herein, the phrase "side effects" refers to undesired events occurring as a result of the traditional use of the inhibitors of the invention. "Side effects" of traditional use of the MTP inhibitors include, without limitation, steatorrhea, abdominal cramping, distention, elevated liver function tests, fatty liver; hepatic fat build up, polyneuropathy, peripheral neuropathy, rhabdomyolysis, arthralgia, myalgia, chest pain, rhinitis, dizziness, arthritis, peripheral edema, gastroenteritis, liver function tests abnormal, colitis, rectal hemorrhage, esophagitis, eructation, stomatitis, biliary pain, cheilitis, duodenal ulcer, dysphagia, enteritis, melena, gum hemorrhage, stomach ulcer, tenesmus, ulcerative stomatitis, hepatitis, pancreatitis, cholestatic jaundice, paresthesia, amnesia, libido decreased, emotional lability, incoordination, torticollis, facial paralysis, hyperkinesia, depression, hypesthesia, hypertonia, leg cramps, bursitis, tenosynovitis, myasthenia, tendinous contracture, myositis, hyperglycemia, creatine phosphokinase increased, gout, weight gain, hypoglycemia, anaphylaxis, angioneurotic edema, and bullous rashes (including erythema multiforme, Stevens-Johnson syndrome, and toxic epidermal necrolysis). In some embodiments, side effects are partially eliminated. As used herein, the phrase partially eliminated refers to a reduction in the severity, extent, or duration of the side effect of at least 25%, 50%, 75%, 85%, 90%, or preferably 95%. In some embodiments, side effects are completely eliminated. Those skilled in the art are credited with the ability to detect and grade the severity, extent, or duration of side effects as well as the degree of amelioration of a side effect. In some embodiments, two or more side effects are ameliorated.

In some embodiments, the methods of the present invention minimize GI side effects or hepatobiliary side effects. In some embodiments, the methods minimize at least one of steatorrhea, abdominal cramping, distention, elevated liver function tests, minor fatty liver; hepatic fat build up, polyneuropathy, peripheral neuropathy, rhabdomyolysis, arthralgia, myalgia, chest pain, rhinitis, dizziness, arthritis, peripheral edema, gastroenteritis, liver function tests abnormal, colitis, rectal hemorrhage, esophagitis, eructation, stomatitis, biliary pain, cheilitis, duodenal ulcer, dysphagia, enteritis, melena, gum hemorrhage, stomach ulcer, tenesmus, ulcerative stomatitis, hepatitis, pancreatitis, cholestatic jaundice, paresthesia, amnesia, libido decreased, emotional lability, incoordination, torticollis, facial paralysis, hyperkinesia, depression, hypesthesia, hypertonia, leg cramps, bursitis, tenosynovitis, myasthenia, tendinous contracture, myositis, hyperglycemia, creatine phosphokinase increased, gout, weight gain, hypoglycemia, anaphylaxis, angioneurotic edema, and bullous rashes (including erythema multiforme, Stevens-Johnson syndrome, and toxic epidermal necrolysis).

In some embodiments, minimization of one or more side effects occurs within 2 weeks of initiation of treatment. In some embodiments, minimization of the one or more side effects occurs within 3 weeks of initiation of treatment.

In some embodiments the minimization of the side effect is determined by assessing the grade, severity, extent, or duration by subject questionnaire.

The present invention also provides methods for inhibiting MTP in a subject while reducing side effects comprising administering to the subject an amount of an MTP inhibitor effective to inhibit MTP. In some embodiments, the MTP inhibitor is administered orally.

The present invention further provides a kit for treating a disorder associated with hyperlipidemia and/or hypercholesterolemia in a subject. In some embodiments the kit comprises at least three sets of dosage units of an MTP inhibitor, wherein a first set of dosage units provides 0.03 mg/kg/day for a first interval, a second set of dosage units provides 0.1 mg/kg/day for a second interval, and a third set of dosage units provides 0.3 mg/kg/day for a third interval; and b) instructions for use. In some embodiments, the kit further comprises a fourth set of dosage units, said fourth set providing 1.0 mg/kg/day for a fourth interval. In some embodiments, the kit further comprises a container for storing the sets of dosage units according to a schedule for administration.

In some embodiments, the kit comprises a first set of dosage units providing 6.25 mg/day for a first interval, a second set of dosage units providing 12.5 mg/day for a second interval, a third set of dosage units providing 25 mg/day for a third interval, a fourth set of dosage units providing 37.5 mg/day for a fourth interval, and a fifth set of dosage units providing 50 mg/day for a fifth interval.

Each set of dosage units comprises sufficient dosage units to administer a desired dosage to the subject for the duration of the period for the specific dose. For example, if a dosage level of 25 mg/day is to be administered to the subject for 2 weeks, the set of dosage units for the 25 mg/day may include 14 dosage units of 25 mg. Alternatively, the set may include 70 dosage units of 5 mg.

In some embodiments the kit further comprises one or more further lipid modifying compounds for the treatment of a disorder associated with hyperlipidemia and/or hypercholesterolemia.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

The dose administered may be adjusted according to age, weight and condition of the patient, as well as the route of administration, dosage form and regimen and the desired result. In some embodiments, doses administered to the subject are titrated until a desired endpoint is reached.

Preparation and formulations of the inhibitors are disclosed infra, supra, and in Canadian Patent Application Ser. No. 2,091,102; U.S. application Ser. No. 117,362; WO 92/26205 published Aug. 29, 1996; U.S. application Ser. No. 472,067, filed Jun. 6, 1995; U.S. application Ser. No. 548, 811, filed Jan. 11, 1996; U.S. provisional application Ser. No. 60/017,224, filed May 9, 1996; U.S. provisional application Ser. No. 60/017,253, filed May 10, 1996; U.S. provisional application Ser. No. 60/017,254, filed May 10, 1996; U.S. provisional application Ser. No. 60/028,216, filed Oct. 1, 1996; U.S. Pat. No. 5,595,872, U.S. Pat. No. 5,712,279; U.S. Pat. No. 5,739,135; U.S. Pat. No. 5,789,197, U.S. Pat. No. 5,883,109, and U.S. Pat. No. 6,066,653. All of the above, including structures, are incorporated herein by reference.

For oral administration, a satisfactory result may be obtained employing the MTP inhibitor in a daily amount within the range of from about 0.01 mg/kg to about 100 mg/kg and preferably from about 0.1 mg/kg to about 75 mg/kg, one to four times daily.

For parenteral administration, the MTP inhibitor may be employed in a daily amount within the range of from about 0.005 mg/kg to about 10 mg/kg and preferably from about 0.005 mg/kg to about 8 mg/kg, one to four times daily.

Additional lipid modifying compounds, when present, may be employed in dosages normally employed as indicated in the Physician's Desk Reference, for each of such agents such as in an amount within the range of from about 2 mg to about 7500 mg, from about 2 mg to about 4000 mg, or from about 10 mg to about 5000 mg.

The MTP inhibitor and other lipid modifying compounds may be employed together in the same oral dosage form or in separate oral dosage forms taken at the same time.

The compositions described above may be administered in the dosage forms as described above in single or divided doses of one to four times daily.

Dosage units including tablets, capsules and caplets, of various sizes can be prepared, e.g., of about 2 to 10000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

In some embodiments, the MTP inhibitor and other lipid modifying compounds are provided in the same dosage unit in the form of a divisible dosage unit. For example, in some embodiments a scored tablet may provide the dosage unit. Under the direction of a physician or other medical professional, the subject may be directed to take one portion of the dosage unit, wherein the one portion will provide the desired dosage level for given interval. At the following interval, the patient may be instructed to take two or more portions of the dosage unit wherein the two or more portions will provide the desired dosage level for that interval.

Liquid formulations can also be prepared by dissolving or suspending one or the combination of active substances in a conventional liquid vehicle acceptable for pharmaceutical administration so as to provide the desired dosage in one to four teaspoonsfuls.

Such dosage forms can be administered to the patient on a regimen of one to four doses per day.

According to some embodiments, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of MTP inhibitors and other lipid modifying compounds are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the carrier, glycerol as solubilizer, sucrose as sweetening agent, methyl and propyl parabens as preservatives, a dye and a flavoring such as cherry or orange.

Some of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the acid lipase deficiency exists. Sustained release forms of such formulations which may provide such amounts biweekly, weekly, monthly and the like may also be employed.

The following examples are meant to illustrate the invention and are not to be construed to limit the invention in any way. Those skilled in the art will recognize modifications that are within the spirit and scope of the invention.

EXAMPLES

Example 1

Formulations suitable for oral administration are prepared as described below.

Capsules containing 1 mg MTP inhibitor BMS 201,038 and capsules containing 50 mg BMS 201,038 are produced from the following ingredients.

|  | 1 mg capsule Amt (mg/capsule) | 50 mg capsule Amt (mg/capsule) |
| --- | --- | --- |
| BMS-201038* | 1.1 | 56.9 |
| Lactose, Hydrous, NF | ca. 30.2 | ca. 99.9 |
| Lactose, Anhydrous, NF | 47.3 | 0.0 |
| Microcrystalline Cellulose, NF | 10.0 | 50.0 |
| Pregelatinized Starch, NF | 5.0 | 25.0 |
| Sodium Starch Glycolate, NF | 5.0 | 12.5 |
| Colloidal Silicon Dioxide, NF | 1.0 | 5.0 |
| Magnesium Stearate, NF | 0.3 | 0.6 |
| Purified Water, USP or | q.s. | q.s. |
| Water for Injection, USP | q.s. | q.s. |
| Gray, Opaque, Size #0 | One Capsule | One Capsule |
| Total Fill Weight | 100.0 | 250.0 |

*In the 1 mg capsule this amount is expressed in terms of the amount of methane sulfonic acid salt per capsule at 100% potency. In the 50 mg capsule, this amount is expressed in terms of the free base This is equivalent to 1 mg and 50 mg (1 mg capsule and 50 mg capsule, respectively) of the free base.

The MTP inhibitor BMS 201,038, and colloidal silicon dioxide are blended in a suitable blender with lactose hydrous, microcrystalline cellulose, pregelatinized starch and a portion of sodium starch glycolate. The resulting blend is wet granulated with water. The wet granulation is dried in a suitable dryer. The remaining portion of sodium starch glycolate is added to the granulation and mixed therein. Magnesium stearate is added to the granulation and mixed therein. The resulting blend is filled into capsules.

Example 2

Pravastatin tablets (10, 20 or 40 mg as described in the 2004 PDR) and MTP inhibitor (BMS 201,238) tablets may be administered as a combination in accordance with the teachings of the present invention. In addition, the pravastatin and MTP inhibitor tablets may be ground up into powders and used together in a single capsule.

Example 3

Simvastatin tablets (10, 20 or 40 mg as described in the 2004 PDR) and MTP inhibitor (BMS 201,238) tablets may be administered as a combination in accordance with the teachings of the present invention. In addition, the simvastatin and MTP inhibitor tablets may be ground up into powders and used together in a single capsule, caplet or tablet.

Example 4

Ezetimibe tablets (10 mg as described in the 2004 PDR) and MTP inhibitor (BMS 201,238) tablets may be administered as a combination in accordance with the teachings of the present invention. In addition, the ezetimibe and MTP inhibitor tablets may be ground up into powders and used together in a single capsule, caplet or tablet.

Example 5

Tablets containing 500 mg clofibrate by itself or in combination with 10 mg BMS 201,038 may be employed in separate dosage forms or combined in a single capsule form.

Example 6

To evaluate pharmacodynamic readouts of treatment according to the present invention, the effects of treatment with BMS-201038 at 4 dose levels (0.03, 0.1, 0.3, and 1.0 mg/kg body weight) on nutritional status, hepatic fat content and pulmonary function can be determined by:
  (a) Hepatic fat content as measured by MRI\nuclear magnetic resonance spectroscopy (NMRS);
  (b) Pulmonary function as measured by spirometry with DLCO;
  (c) Nutritional status as measured by serum levels of fat soluble vitamins A, D, and E;
  (d) international normalized ratio (INR) to evaluate vitamin K status; and plasma phospholipid inoleic acid, arachidonic acid, alpha linolenic acid and eicosapentaenoic acid by gas liquid chromatography to assess essential fatty acid intake.

Example 7

Twenty (20) subjects are randomized in a 3:1 ratio to BMS-201038 (n=15) or placebo (n=5) in a double-blind fashion for 11-15 weeks depending on weight as described below. At the end of 11 or 15 weeks, BMS-assigned subjects will continue taking the maximum tolerated dose for the remaining study (through week 39). For BMS-201038-treated patients, study drug will be initiated at 6.25 mg/d for 1 week and then will be titrated up to 12.5 mg/day for 2 weeks followed by 25 mg/day for 4 weeks and then to 50 mg/day for 4 weeks. BMS-201038 treated subjects whose weight is between 62.5 and 74.9 kg will titrate up to 62.5 mg/day for an additional 4 weeks. BMS-201038-treated subjects whose weight is ≥75 kg, will titrate up from 50 mg to 75 mg/day for an additional 4 weeks. Subjects who weight is <62.5 kg will remain at 50 mg/d (or the maximum tolerated dose) for the remaining 28 weeks. Subjects who titrate up to 62.5 mg/d or 75 mg/day will remain at this dose (or the maximum tolerated dose) for the remaining 24 weeks.

Subjects randomized to placebo will take matching placebo for 15 weeks. After this time period, placebo-treated subjects will start taking BMS-201038 following the same schedule as outlined above for the original BMS-201038-treated subjects. After the dose titration schedule is complete at week 26 or 30 depending on weight, subjects will take the maximum tolerated dose for the remaining study (through week 39) so that the entire study for all subjects will be 39 weeks in duration.

Example 8

The tolerability and thus the effectiveness of BMS-201038 appears to be dependent on the dosing regimen. In a phase II study using BMS-201038 in patients with primary hypercholesterolemia, a dosage of 25 mg per day for 4 weeks produced clinically significant gastrointestinal (GI) steatorrhea, abdominal cramping and distention) and statistically significant hepatobiliary (elevated liver function tests and minor fatty liver) symptoms in some patients receiving study drug. It appeared that the degree of both GI-related symptoms and hepatic fat were in part due to the study design, particularly the dosing regimen. BMS-201038 is a potent inhibitor of both intestinal and hepatic microsomal triglyceride transfer protein (MTP). While lack of adequately controlling dietary fat intake most likely contributed to GI-related symptoms, it is possible that providing a starting dose of 25 mg/day also contributed. Starting at a low dose and titrating up slowly may improve GI-related tolerability as well as provide time for the liver to adjust to the inhibition of MTP, perhaps decreasing hepatic fat build up. This theory was applied in designing a study investigating the safety, tolerability and efficacy of BMS-201038 in patients with homozygous familial hypercholesterolemia (hoFH).

Six patients with hoFH were enrolled and completed the study per protocol. Subjects received once daily dosing of 4 doses of BMS-201038 (0.03, 0.1, 0.3 and 1.0 mg/kg) for 4 weeks at each dose. We chose an initial low dose (0.03 mg/kg) that while not expecting to be efficacious, would be a dose that would be expected to be safe and well tolerated (~2.1 mg in the 70 kg man). The remaining three doses were chosen by calculating ½ log units of the previous dose. We picked an upper dose of 1 mg/kg based on data from the animal study by Wetterau and colleagues revealing greater than 80% LDL cholesterol reduction using 10 mg/kg, with an $ED_{50}$ of 1.9 mg/kg. All 6 subjects tolerated the drug up to the maximal 1 mg/kg dose with little to no steatorrhea. Although all subjects had evidence of dose-dependent increases in hepatic fat by NMRS, the increase from baseline to 4 weeks on 1 mg/kg was varied with a range of 3-37%. Three of 6 subjects experienced substantial increases in liver transaminases, but only 1 subject had a persistent increase that required a temporary dose reduction. This subject also had the greatest increase in hepatic fat which may have been exacerbated by the large consumption of alcohol on a regular basis. At the two highest doses, the mean percent changes in lipids among the 6 subjects were: total cholesterol −30±9% and −58±8.5%, non-HDL cholesterol −31±9% and −60±8.8%, and apoB −15±16% and −55±13%, respectively.

These data indicate that symptoms of steatorrhea and hepatic fat can be significantly reduced by initiating a low dose with a gradual up titration.

Each of the patents, patent applications, references and publications described herein is hereby incorporated by reference in its entirety.

Various modifications of the invention, in addition to those described herein, will be apparent to those of skill in the art in view of the foregoing description. Such modifications are also intended to fall within the scope of the appended claims.

What is claimed is:

1. A method of treating a subject suffering from hyperlipidemia or hypercholesterolemia, the method comprising orally administering to the subject an effective amount of an MTP inhibitor, wherein said administration comprises three step-wise, increasing dose levels of the MTP inhibitor, wherein each dose level is 50% of the immediately following dose level, wherein the third dose level is about 0.2 to about 0.59 mg/kg/day, and wherein the MTP inhibitor is N-(2,2,2-trifluoroethyl)-9-[4-[4-[[[4'-(trifluoromethyl) [1,1'-biphenyl]-2-yl] carbonyl] amino]-1-piperidinyl] butyl]-9H-fluorene-9-carboxamide, methanesulfonate; wherein each dose level is administered for a period of about 7 to about 35 days; and wherein the subject suffering from hyperlipidemia or hypercholesterolemia has homozygous familial hypercholesterolemia.

2. The method of claim 1, wherein the first dose level is administered for about 2 weeks and the second and third dose levels are each administered for about 4 weeks.

3. The method of claim 1, wherein administration further comprises a fourth dose level, wherein the third dose level is 50% of the fourth dose level.

4. The method of claim 3, upon administration, the LDL-cholesterol of the subject is reduced by at least 25% compared to pre-treatment levels.

5. The method of claim 1, wherein upon administration the subject has reduced symptoms of steatorrhea and/or hepatic fat as compared to a subject administered a starting dose of 25 mg/day of the MTP inhibitor.

6. A method of treating a subject suffering from hyperlipidemia or hypercholesterolemia the method comprising administering to the subject an effective amount of an MTP inhibitor, wherein said administration comprises at least three step-wise, increasing dose levels of the MTP inhibitor, wherein each dose level is 50% of the immediately following dose level, wherein the second dose level is about 0.06 mg/kg/day to about 0.19 mg/kg/day, wherein the MTP inhibitor is N-(2,2,2-trifluoroethyl)-9-[4-[4-[[[4'-(trifluoromethyl) [1,1'-biphenyl]-2-yl] carbonyl] amino]-1-piperidinyl] butyl]-9H-fluorene-9-carboxamide, methanesulfonate, wherein each dose level is administered for a period of about 7 to about 35 days, and wherein the subject suffering from hyperlipidemia or hypercholesterolemia has homozygous familial hypercholesterolemia.

7. The method of claim 6, wherein the first dose level is administered for about 2 weeks and the second and third dose levels are each administered for about 4 weeks.

8. The method of claim 6, wherein said increasing dose levels further comprise a fourth dose level, wherein the third dose level is 50% of the fourth dose level.

9. The method of claim 8, upon administration, the LDL-cholesterol of the subject is reduced by at least 25% compared to pre-treatment levels.

10. The method of claim 6, wherein upon administration the subject has reduced symptoms of steatorrhea and/or hepatic fat as compared to a subject administered a starting dose of 25 mg/day of the MTP inhibitor.

11. A method of treating a subject suffering from hyperlipidemia or hypercholesterolemia, the method comprising administering to the subject an effective amount of an MTP inhibitor, wherein said administration comprises three stepwise, increasing dose levels of the MTP inhibitor, wherein each dose level is no more than 50% of the immediately following dose level, and wherein the first dose level is about 0.02 to about 0.059 mg/kg/day, the second dose level is about 0.06 mg/kg/day to about 0.19 mg/kg/day, and the third dose level is about 0.2 to about 0.59 mg/kg/day; wherein the MTP inhibitor is N-(2,2,2-trifluoroethyl) -9-[4-[4[[[4'-(trifluoromethyl)[1,1'-biphenyl]-2-yl] carbonyl] amino]-1-piperidinyl] butyl]-9H-fluorene-9-carboxamide, methanesulfonate; wherein each dose level is administered for a period of about 7 to about 35 days; and wherein the subject suffering from hyperlipidemia or hypercholesterolemia has homozygous familial hypercholesterolemia.

12. The method of claim 11, wherein said increasing dose levels further comprise a fourth dose level, wherein the fourth dose level is about 0.6 to about 2.0 mg/kg/day.

13. The method of claim 11, upon administration, the LDL-cholesterol of the subject is reduced by at least 25% compared to pre-treatment levels.

14. The method of claim 11, wherein upon administration the subject has reduced symptoms of steatorrhea and/or hepatic fat as compared to a subject administered a starting dose of 25 mg/day of the MTP inhibitor.

* * * * *